United States Patent
Xie et al.

(10) Patent No.: US 11,969,286 B2
(45) Date of Patent: *Apr. 30, 2024

(54) SYSTEMS AND METHODS FOR AUTOMATIC DETECTION AND VISUALIZATION OF TURBULENT BLOOD FLOW USING VECTOR FLOW DATA

(71) Applicant: KONINKLIJKE PHILIPS N.V., Eindhoven (NL)

(72) Inventors: Hua Xie, Cambridge, MA (US); Shiying Wang, Melrose, MA (US); Sheng-Wen Huang, Ossining, NY (US); Francois Guy Gerard Marie Vignon, Andover, MA (US); Keith William Johnson, Lynnwood, WA (US); Liang Zhang, Issaquah, WA (US); David Hope Simpson, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/992,423

(22) Filed: Nov. 22, 2022

(65) Prior Publication Data

US 2023/0085700 A1 Mar. 23, 2023

Related U.S. Application Data

(63) Continuation of application No. 16/616,753, filed as application No. PCT/EP2018/063756 on May 25, 2017, now Pat. No. 11,534,131.

(Continued)

(51) Int. Cl.
*A61B 8/06* (2006.01)
*A61B 8/00* (2006.01)
*A61B 8/08* (2006.01)

(52) U.S. Cl.
CPC .............. *A61B 8/06* (2013.01); *A61B 8/461* (2013.01); *A61B 8/469* (2013.01); *A61B 8/5246* (2013.01)

(58) Field of Classification Search
CPC ........... A61B 8/06; A61B 8/461; A61B 8/469; A61B 8/5246
See application file for complete search history.

(56) References Cited

U.S. PATENT DOCUMENTS

| 5,622,173 A | 4/1997 | Bisson et al. |
| 6,859,659 B1 | 2/2005 | Jensen |

(Continued)

FOREIGN PATENT DOCUMENTS

| JP | H0833625 A | 2/1996 |
| JP | 2003116850 A | 4/2003 |

(Continued)

OTHER PUBLICATIONS

BK Ultrasound Manual (www.frankshospitalworkshop.com/equipment/documents/ultrasonographs/user_manuals/BK%203000,%205000%20Ultrasound%20System%20-%20Advanced%20user%20manual.pdf; Nov. 2016).*

(Continued)

*Primary Examiner* — Carolyn A Pehlke

(57) ABSTRACT

A system for visualization and quantification of ultrasound imaging data according to embodiments of the present disclosure may include a display unit, and a processor communicatively coupled to the display unit and to an ultrasound imaging apparatus for generating an image from ultrasound data representative of a bodily structure and fluid flowing within the bodily structure. The processor may be configured to estimate axial and lateral velocity components of the fluid flowing within the bodily structure, determine a plurality of flow directions within the image based on the axial and lateral velocity components, differentially encode (Continued)

the flow directions based on flow direction angle to generate a flow direction map, and cause the display unit to concurrently display the image including the bodily structure overlaid with the flow direction map.

9 Claims, 15 Drawing Sheets

Related U.S. Application Data

(60) Provisional application No. 62/510,819, filed on May 25, 2017.

(56) References Cited

U.S. PATENT DOCUMENTS

| | | |
|---|---|---|
| 9,170,330 B2 | 10/2015 | Haugaard et al. |
| 9,204,858 B2 | 12/2015 | Pelissier et al. |
| 2006/0052698 A1 | 3/2006 | Loupas |
| 2011/0317881 A1 | 12/2011 | Bonnefous et al. |
| 2013/0150717 A1 | 6/2013 | Sato |
| 2015/0141824 A1 | 5/2015 | You et al. |
| 2015/0141832 A1 | 5/2015 | Yu et al. |
| 2016/0015366 A1 | 1/2016 | Haugaard et al. |
| 2016/0174931 A1* | 6/2016 | Pelissier .................. A61B 8/08 600/454 |
| 2019/0365354 A1* | 12/2019 | Du .......................... A61B 8/145 |

FOREIGN PATENT DOCUMENTS

| | | |
|---|---|---|
| WO | 2013046089 A1 | 4/2013 |
| WO | 2014140657 A1 | 9/2014 |
| WO | 2016139506 A1 | 9/2016 |
| WO | 2018177986 A1 | 10/2018 |

OTHER PUBLICATIONS

Angelelli et al., "Live Ultrasound-Based Particle Visualization of Blood Flow in the Heart"; Proceedings of the 30th Spring Conference on Computer Graphics, pp. 13-20, 2014.
Evans et al., "Ultrasonic Colour Doppler Imaging"; Interface Focus (2011), vol. 1, pp. 490-502.
Jensen et al: "Recent Advances in Blood Flow Vector Velocity Imaging"; 2011 IEEE International Ultrasonics Symposium, 2011, pp. 262-271.
Jensen et al: "Ultrasound Vector Flow Imaging-Part I: Sequential Systems"; IEEE Transactions on Ultrasonics, Ferroelectrics, and Frequency Control; vol. 63, No. 11, Nov. 2016, pp. 1704-1721.
International Search Report and Written Opinion for PCT/EP2018/063756; dated Sep. 11, 2018, 16 pages.
By et al., "Vector projectile imaging: time-resolved dynamic visualization of complex flow patterns", Ultrasound in Medicine & Biology, 2014, vol. 40 No. 9, pp. 2295-2309.

* cited by examiner

SYSTEMS AND METHODS FOR AUTOMATIC DETECTION AND VISUALIZATION OF TURBULENT BLOOD FLOW USING VECTOR FLOW DATA

RELATED APPLICATION

This application is a continuation application of co-pending U.S. patent application Ser. No. 16/616,753, filed on Nov. 25, 2019, which in turn is the U.S. National Phase application under 35 U.S.C. § 371 of International Application No. PCT/EP2018/063756, filed on May 25, 2018, which claims the benefit of U.S. Provisional Patent Application No. 62/510,819, filed on May 25, 2017. These applications are hereby incorporated by reference herein.

TECHNICAL FIELD

The present disclosure pertains to ultrasound systems and methods for automatic detection and visualization of turbulent blood flow using vector flow imaging.

BACKGROUND

Normal cardiovascular blood flow is generally laminar. In the presence of diseases such as vessel narrowing, plaque build-up, and heart valve malfunction, flow may exhibit turbulent and disorganized patterns in space and time. Ultrasound Doppler flow imaging has been used as a non-invasive diagnostic tool for assessment and quantification of blood flow hemodynamics. In a typical Doppler exam, two-dimensional (2D) Color or Power Doppler imaging is first used to visually assess vessel patency, vessel stenosis, or intra-cardiac flow, which may be followed with Spectral Doppler for further quantitative measurement at specific sites. Spectral Doppler may provide higher accuracy velocity measurements. Though remaining as a widely used tool, conventional Doppler imaging is angle-dependent and can only provide one-dimensional velocity estimation along the axial direction, with the flow being characterized as either away or toward the acoustic beams. Conventional Doppler cannot resolve the true flow direction and thus, introduces measurement bias in velocity. This limits its application in accurate flow assessment and quantification.

SUMMARY

The present invention provides systems and methods for automatic detection and visualization of turbulent blood flow utilizing vector flow imaging data. In particular embodiments, systems and method according to the present invention use the vector flow data to determine localized variances of flow direction and speed, and display those variances in various ways on the user interface, for example in histogram displays. The determination of specific points to be localized and for which flow direction and/or speed is provided may be responsive to user inputs (e.g., a user selected region of interest) or automatic (e.g., responsive to a determination by the system of a suspicious region). As a result, techniques of the invention provide enhanced and more accurate flow pattern characterization and turbulent flow visualization to assist physicians in the diagnosis and monitoring of various cardiovascular conditions including artery stenosis and cardiac disorders.

A system for visualization and quantification of ultrasound imaging data according to embodiments of the present disclosure may include a display unit, and a processor communicatively coupled to the display unit and to an ultrasound imaging apparatus for generating an image from ultrasound data representative of a bodily structure and fluid flowing within the bodily structure. The processor may be configured to estimate axial and lateral velocity components of the fluid flowing within the bodily structure, determine a plurality of flow directions within the image based on the axial and lateral velocity components, differentially encode the flow directions based on flow direction angle to generate a flow direction map, and cause the display unit to concurrently display the image including the bodily structure overlaid with the flow direction map.

In some embodiments, processor may be configured to encode the flow directions using a color key including at least three distinct colors and to cause the display to display a visual representation of the color key. Each of the three distinct colors may be assigned to a specific flow direction. For example, a nominal zero orientation of flow may be selected, such as an orientation from the left to the right of the image and any velocity vectors aligned with this orientation may be referred to as having a zero-delta orientation from the nominal. In one example, in which the three distinct color use are the primary colors red, blue and yellow, the color red may be assigned to velocity vectors which have are angle 0 degrees to the nominal, that is, in this example a purely lateral velocity vector (i.e., having zero axial component) indicative of flow in a direction from left to right of the image. The color blue may then be assigned to an angle delta of 180 degrees, that is, in this example a purely lateral velocity vector (i.e., having zero axial component) indicative of flow in a direction from right to left of the image, and yellow may be assigned to either an angle delta of +90 or to an angle delta of −90, which in this example would be a purely axial velocity vector (i.e., having a zero lateral component) indicative of flow in a direction either from bottom to top of the image or from top to bottom of the image, respectively. The colors corresponding to all flow directions between purely lateral and/or axial velocity vectors may be assigned by generating a color gradient (e.g., using linear interpolation) between the primary colors. Any other combination of distinct colors and gradients therebetween may be used for differentially encoding the flow directions in color. In some embodiments, the visual representation of the color key may be in the form of a color bar which may be configured to show a color gradient and corresponding fluid flow directions. In other embodiments, the visual representation of the color key may be in the form of a color wheel. The color wheel may be centered on an x-y coordinate frame with the positive x-axis aligned with the 0 degrees or nominal flow direction and the positive y-axis aligned with the +90 degree relative to nominal flow direction. The color gradient may be superimposed onto the color wheel to provide a visual indication of colors corresponding with the different flow directions.

In some embodiments, the processor may be configured to receive a selection of a region of interest (ROI) within the flow region and cause the display unit to display additional quantitative information about the flow directions within the ROI. In some embodiments, the selection of the ROI received by the processor may be responsive to user inputs. For example, the user may designate a sub-region within the flow region, such as by clicking on and dragging a cursor over a portion of the color map display to indicate a potentially suspicious region visually identified by the user based on the color map display. In other embodiments, the selection of the ROI received by the processor may be responsive to automatic identification of a suspicious region by the processor. For example, the processor may be configured to perform statistical analysis on the flow directions obtained from the vector flow analysis and may be configured to identify a sub-region within the flow region that is exhibiting turbulent flow. The ROI may be automatically selected by the processor, e.g., to correspond to the identified sub-region of turbulent flow. Once a suspicious region has been identified and an ROI selected by the processor, the processor may be further configured to provide a visual indication of the ROI in the image. In some embodiments, the user interface may provide user controls to enable the user to move and/or resize the ROI, for example an ROI automatically identified by the processor.

In some embodiments, upon identification of an ROI (e.g., a region corresponding to a suspicious region), the processor may be configured to cause the display unit to display additional quantitative information about the ROI, such as one or more histograms. As described herein, the processor may be configured to perform statistical analysis using the multi-directional velocity data and may be configured to cause the display to display a histogram of the flow directions within the ROI or a statistical measure of variability of the flow directions within the ROI. In some embodiments, the processor may be configured to cause the display to display a two-dimensional (2D) histogram displaying at least two of the flow directions at every pixel within the ROI, velocity magnitudes at every pixel within the ROI, and a statistical measure of variability of either the flow directions or velocity magnitudes associated with the ROI. In some embodiments, the histograms may be displayed concurrently with flow visualization information (e.g., overlay images including a vector flow map or a color map of flow directions), while in other embodiments, the histograms may be displayed and/or output to a report regardless of whether visualization information of the fluid flow is displayed.

In some embodiments, the flow direction map, histogram displays and/or vector flow imaging information may be updated in real time. In further embodiments, the processor may be configured to generate the histogram using time-averaged values, for example averaged over a pre-programmed or user-selected period of time such as over a given portion of the cardiac cycle (e.g., the duration of systole) or a fraction thereof. In the case of the latter, the system may receive an ECG signal to determine the period of time corresponding to the phase of the cardiac cycle over which data will be averaged.

In some embodiments, the processor may be configured to cause the display unit to concurrently display two or more ultrasound images and in some instances additionally, quantitative information about the fluid flow. For example, the image including the flow direction map may be a first image, which may be displayed concurrently with an image including vector flow imaging (VFI) data also based on the axial and lateral velocity components. Similar to the image with the flow direction may, the VFI data may be overlaid on another background B-mode image of the bodily structure. The displays containing the flow direction may and the VFI data, for example when displaying the images in real-time, may be synchronized such that corresponding frames are displayed in each of the two vector flow visualization displays. In some embodiments, the visualization and quantification system described herein may be incorporated with the ultrasound imaging apparatus. That is the processor and display units may be components of an ultrasound imaging system which also includes or is configured to be operably coupled to an ultrasound probe for acquiring the ultrasound image data.

A system according to further embodiments of the present disclosure may include a display unit and a processor communicatively coupled to the display unit and to an ultrasound imaging apparatus for generating an image from ultrasound data representative of a bodily structure and fluid flowing within the bodily structure. The processor may be configured to estimate axial and lateral velocity components of the fluid flowing within the bodily structure, determine a plurality of flow directions within the image based on the axial and lateral velocity components, the flow directions each defining an angle. The processor may be further configured to automatically identify a flow sub-region comprising flow directions of statistical significance and to cause the display unit to display the image including the bodily structure and the identified statistically significant flow sub-region. In some embodiments, the flow sub-region that includes flow directions of statistical significance may be a region or ROI within the flow region that includes flow directions associated with a moving average and/or standard deviation that exceeds or meets a threshold. In some embodiments, the processor may be further configured to concurrently display a histogram of the flow directions within the automatically identified sub-region. In embodiments, the histogram may be a 2D histogram or a 3D histogram of flow directions and flow direction velocities within the sub-region.

A method for displaying ultrasound imaging data according to some embodiments may include generating an image from ultrasound data representative of a bodily structure and fluid flowing within the bodily structure, estimating axial and lateral velocity components of the fluid flowing within the bodily structure, determining a plurality of flow directions within the image based on the axial and lateral velocity components, differentially encoding the flow directions based on flow direction angle to generate a flow direction map, and displaying the image including the bodily structure overlaid with the flow direction map. In some embodiments, the method may include receiving a selection of a region of interest (ROI) within the flow region and displaying additional quantitative information about the flow directions within the ROI. The selection of the ROI may be responsive to user input, or it may be automatically selected by the system. In some embodiments of the method, the processor may perform statistical analysis on the flow directions, and the ROI may be automatic selected by the processor based on the statistical analysis. In some embodiments, the displaying additional quantitative information about the flow directions within the ROI may include displaying at least two of the flow directions for pixels within the ROI, velocity magnitudes for pixels within the ROI, and a statistical measure of variability of either the flow directions or velocity magnitudes associated with the ROI. In some embodiments, the displaying additional quantitative information may include displaying a 3D histogram, which plots for example any two of the flow directions at every pixel in the ROI, the velocity magnitudes at the corresponding pixels, or a statistical measure of variability of either the flow directions or velocity magnitudes associated with the ROI. Other parameters may be quantified and presented to the user, for example in 1D or 2D histograms, based on the beam-angle-independent velocity data. In some embodiments, the method may further include concurrently displaying one or more additional images including a B-mode background image overlaid with vector map based on the beam-angle-independent velocity components.

Any of the methods in accordance with the present disclosure, or steps thereof, may be embodied in non-transitory computer-readable medium comprising executable instructions, which when executed may cause a processor of medical imaging system to perform method or steps embodied therein.

DESCRIPTION

Figure 1:
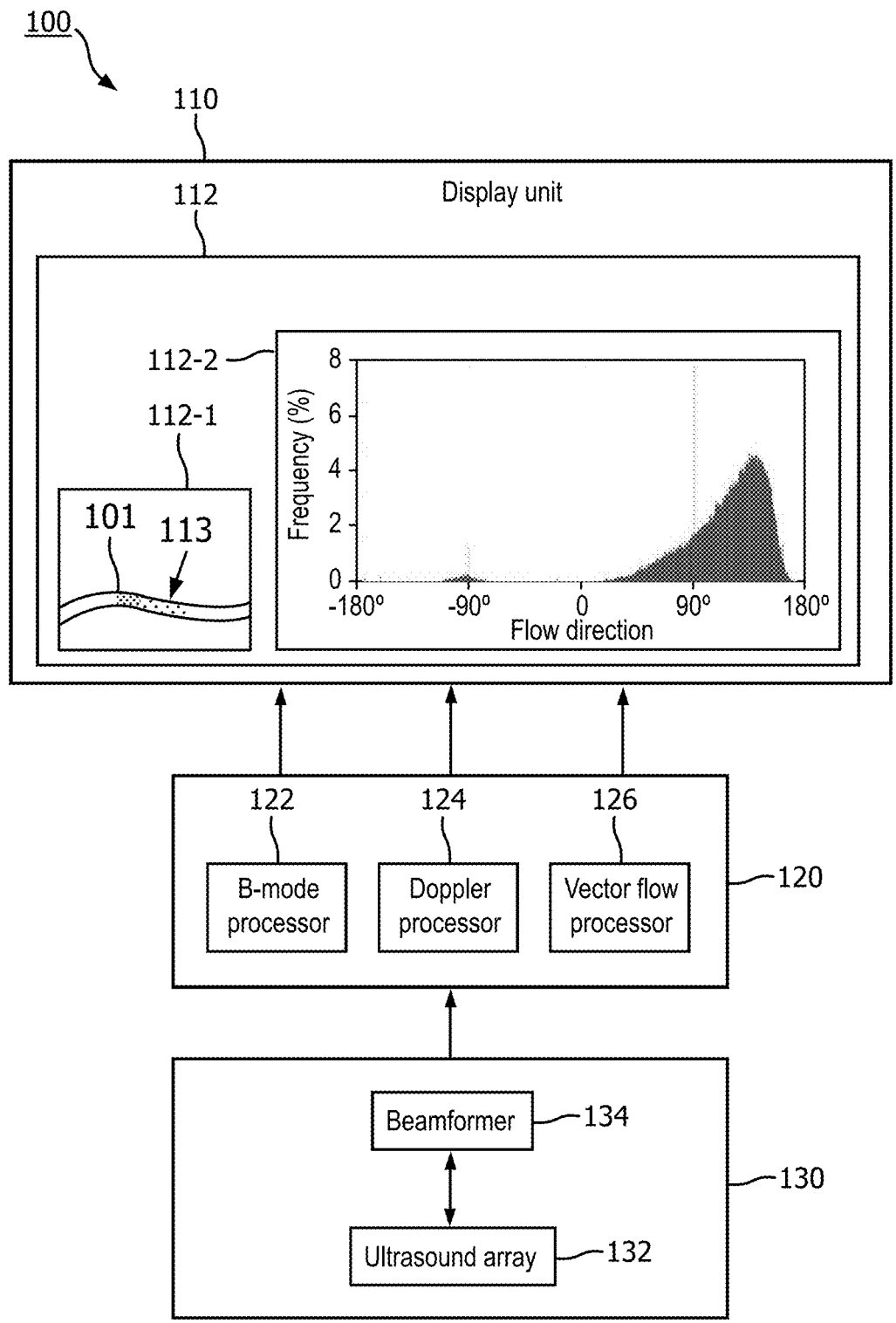
FIG. 1 is block diagram of a visualization and quantification system in accordance with principles of the present inventions.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

Vector flow imaging (VFI) can be used to visualize and quantify complex blood flow measurements in cardiovascular applications for better diagnosis of stenosis and other conditions of the vascular system. Since conventional Doppler ultrasound only allows velocity estimation along the axial direction (i.e., along the beam direction), new vector flow imaging techniques have been introduced to allow multi-directional (also referred to as beam-angle-independent) velocity estimations. Additionally, vector flow imaging techniques may be used to visualize the multi-directional velocity estimates using, for example, fixed-arrow-based, free-arrow-based, or pathlet-based visualization (see e.g., FIG. 3A). For fixed-arrow-based visualization, the magnitude of flow velocity is encoded as color intensity, and is proportional to the length of the arrow. The direction of flow velocity is shown both by the arrow and color. The tail of the arrow is fixed in space. For free-arrow-based visualization, free arrow is used to dynamically track the blood flow. The magnitude of flow velocity is color encoded, and is proportional to the length of the arrow. The direction of flow velocity is indicated by the arrow. In the context of VFI, streamline may be defined as a family of curves that are instantaneously tangent to the velocity vector of the flow, and a pathline can be defined as a family of trajectories that the flow particles would faithfully follow during flow. For pathlets-based (i.e. streamline, pathline) visualization, dynamic curve tracing of the flow trajectory is achieved by curved pathlets. Pathlets can be seen as the short, frontal segments or parts of the pathlines, that start to fade out when distance from the tip exceeds a given threshold, which is defined as the pathlet length. The magnitude of flow velocity is color encoded, and is proportional to the length of the pathlets. The direction of flow velocity is indicated by the moving direction of pathlets. Overall, among the three visualization methods, pathlet-based visualization is the most intuitive method with potential to replace the other visualization methods for VFI.

While an improvement over conventional Doppler imaging, existing implementations of vector flow imaging may still have limitations. For example, in existing fixed-arrow-based visualization techniques, the length of the arrow is not a direct measurement of velocity magnitude and the interpretation of the image may thus be not as intuitive to the user as may be desired. In existing free-arrow-based visualization techniques, the arrows are typically straight lines and may not be good representations of curved trajectories. Additionally, the inclusion of arrowheads for each streamline may clutter the visualization and again, be less intuitive. Also, in existing free-arrow-based and pathlets-based visualizations, neither the coded color map nor the length of the arrow (pathlet) is a direct measurement of velocity magnitude. Consequently, direct measurements and accurate quantification of blood flow are unavailable. Quantitative information about the flow is also generally not available with existing techniques. Additional shortcomings of existing VFI techniques may include the inability to perform point measurements of blood flow at certain locations of interest, which can further limits the capability of VFI to extract detailed spatiotemporal information of blood flow. Examples in accordance with the present disclosure may address one or more of the shortcomings of existing VFI systems and methods.

Blood flow spatiotemporal patterns may change from normal to abnormal in the presence of cardiovascular diseases. Ultrasound Doppler-based flow imaging has been a widely used diagnostic tool to measure and assess blood flow hemodynamics. However, due to its inherent angular dependence, traditional Doppler techniques (e.g., color Doppler) only provide one-dimensional velocity measurement in the beam direction, thus limiting their performance in terms of full resolution of flow direction. In accordance with principles of the present invention, emerging vector flow imaging (VFI) techniques, which overcome the angle-dependency limitation of prior Doppler imaging techniques, may be used to obtain more accurate flow velocity (speed and direction) measurements. The beam-angle-independent velocity information obtained through vector flow imaging can then be used to identify and quantify turbulent blood flow with higher accuracy. Turbulent flow generally exhibits large variation in flow directions as well as speed. Several VFI techniques have been developed, which can overcome the limitations of conventional Doppler by their capability of obtaining beam-angle-independent, also referred to as multi-directional, velocity estimation. For example, techniques such as fixed-arrow-based, free-arrow-based, and pathlet-based visualization may be used in some embodiments of the present disclosure for visualization of fluid flow velocity estimates, as will be further described. The present disclosure pertains to systems and methods which utilize VFI-based techniques for turbulent flow detection and assessment. The features can characterize flow patterns, visualize turbulent flows and assist physicians in diagnosis of artery stenosis, and cardiac disorders.

FIG. 1 shows a block diagram of a system 100 according to embodiments of the present disclosure. A system 100 for visualization and quantification of ultrasound imaging data according to embodiments of the present disclosure may include a display unit 110, and a processor 120 communicatively coupled to the display unit and to an ultrasound imaging apparatus 130 for generating an image from ultrasound data representative of a bodily structure 101 (e.g., a blood vessel) and fluid flowing within the bodily structure. The display unit 120 may be implemented using any type of suitable display technology such as passive or touch-sensitive LCD, LED, or OLED technologies. The ultrasound imaging apparatus 130, also referred to herein as ultrasound scanner, may include an ultrasound array 132 that may be housed in an external or an intravascular probe, and a beamformer 134, which may operate under the control of an imaging controller to direct ultrasound beams and receive ultrasound echoes from a subject (e.g., a patient) using the ultrasound array 132, which are then beam-formed and transmitted to one or more processors for further processing and image generation. In some embodiments, the processor 120 and/or the display unit 110, or components thereof (such as one or more of the processors 122, 124, and 126), may be integrated with the ultrasound imaging apparatus 130, which may for example be any of the ultrasound imaging system, such as the SPRAQ or the EPIQ ultrasound system, provided by PHILIPS. In some examples, the processor 120 may additionally or alternatively be configured to receive ultrasound imaging data, for example imaging data from an imaging session performed prior to visualization and quantification of the data by a clinician, and which has been stored in memory (e.g., memory storage device of a picture archiving and communication system (PACS)) for later access by the processor 120.

The processor 120 may be configured to generate ultrasound imaging data associated with two or more imaging modes (e.g., B-mode, Doppler imaging, Vector Flow imaging, etc.) for display on the display unit 110. To that end, the processor may include a B-mode processor 122 configured to generate B-mode images and a Doppler processor 124 configured to generate Doppler images (e.g., color-flow Doppler, spectral Doppler, and power Doppler such as Color Power Angio (CPA) images). In some examples, images 112-1 may be displayed as overlays of imaging data obtained from multiple imaging modes. For example in duplex (e.g., B-mode/Doppler) imaging, a gray-scale image of the anatomy (i.e., a B-mode image) may be overplayed with color-flow Doppler data to provide, for example, a color-flow Doppler image. In some embodiments, the processor 120 may be configured to generate vector field data including axial and lateral velocity components of the fluid flowing within the bodily structure. To that end, the processor 120 may include a vector flow processor 126 configured to generate beam-angle-independent velocity estimates from the beamformed RF signals received from the imaging apparatus 130. The processor 120 may be further configured to generate vector flow imaging (VFI) data based on the vector field data, which data may be overlaid on background B-mode images similar to B-mode/Doppler duplex imaging.

In accordance with principles of the present invention, the processor 120 may be configured to estimate beam-angle-independent velocities of fluid particles (e.g., axial, lateral, and in the case of 3D imaging elevational, velocity components of the fluid flowing within the bodily structure), also referred to as multi-directional velocity data or vector field data and display one or more images 112-1 including visualization data based on the multi-directional velocity data. The processor 120 may be configured to determine a plurality of flow directions within the image based on the axial and lateral velocity components and to differentially encode the flow directions based on flow direction angle, such as to generate a flow direction map. For example, the direction of flow at any given location within a flow region of the image (e.g., at every pixel within a region of the image defined as the flow region, which may correspond to the region enclosed by the bodily structure) may be obtained from the vector field data and may be used for further visualization and quantification, as described further below. In some examples, the multi-directional velocity data (e.g., axial and lateral velocity components) may then be used to generate a color map 113, e.g., a flow direction map, which encodes in color a parameter obtained from the multi-directional flow data such as the flow directions locations in the flow region. Since the color map of the present disclosure is based on the beam-angle-independent velocity estimates, a more accurate visualization of parameters associated with the flow (e.g., the flow directions and/or quantitative information associated with the flow) may be achieved as would have otherwise been obtainable using conventional Colorflow Doppler which does not provide an accurate flow direction or make quantification of flow parameters possible.

In some embodiments, the processor 120 may be configured to receive a selection of a region of interest (ROI) within the flow region and cause the display unit 110 to concurrently display additional quantitative information about the flow directions within the ROI. The selection of the ROI received by the processor may be responsive to user inputs or responsive to an automatic identification of a region of interest by the processor 120. In some embodiments, upon selection of an ROI, the processor 120 may be configured to cause the display unit 110 to display additional quantitative information 112-2 about the ROI, such as one or more histograms. As described herein, the processor 120 may be configured to perform statistical analysis using the multi-directional velocity data for generating 1D or 2D histograms. A variety of parameters, including the flow direction at each pixel in an ROI, the magnitude at each pixels, or various statistical parameters (e.g., measures of statistical variability such as mean, median, standard deviation, or higher order statistical parameters) may be plotted on a 1D or 2D histogram in accordance with the present invention. For example, the system 100 may display the flow distribution in the format of a histogram of flow direction and/or speed accompanied by statistical analysis (e.g., mean, standard deviation, and/or higher order statistics). The visualization of the vector field data (e.g., the VFI image or the flow direction map image) may be displayed concurrently with the histogram(s) statically or dynamically, in real-time, (e.g., where each of the images and the statistical data plotted in the histogram may be dynamically updated in real time). In other example, the displays may be retrospectives, such as when generated for display on an analysis workstation rather than in real-time on an imaging system. In yet other examples, the images may be retrospective, such as by using a cine loop when an imaging system is in freeze mode.

In some embodiments of the system, after multi-directional velocity data (e.g., axial and lateral velocity components) have been estimated, the processor 120 may be configured to automatically determine a flow sub-region that include flow directions of statistical significance and to cause the display unit to display the image including the bodily structure and the identified statistically significant flow sub-region. That is, in some embodiments, statistical analysis may be used to identify the ROI and additionally, optionally, display a histogram associated with the ROI regardless of whether additional visualization of the flow region (e.g., vector flow map or flow direction color map) are generated and displayed. In some embodiments, the flow sub-region that includes flow directions of statistical significance may be a region or ROI within the flow region that includes flow directions associated with a moving average and/or standard deviation that exceeds or meets a threshold. In some embodiments, the processor 120 may be further configured to concurrently display a histogram of the flow directions within the automatically identified sub-region. The histogram may be a 2D histogram or a 3D histogram of flow directions and flow direction velocities within the sub-region.

In some embodiments, the processor 120 may be configured to cause the display unit 110 to concurrently display two or more ultrasound images 112-1 and in some instances additionally concurrently with the quantitative information (e.g., histogram) about the fluid flow. For example, the image including the flow direction map may be a first image, which may be displayed concurrently with an image including vector flow imaging (VFI) data also based on the axial and lateral velocity components. Similar to the image with the flow direction may, the VFI data may be overlaid on another background B-mode image of the bodily structure. The displays containing the flow direction may and the VFI data, for example when displaying the images in real-time, may be synchronized such that corresponding frames are displayed in each of the two vector flow visualization displays. The selection of an ROI for further quantitative analysis (e.g., statistical analysis and display) may be done, in the case of the user-selected ROI, either by interacting (e.g., clicking and dragging a window) on the flow direction map display or on the VFI display. In some embodiments, the visualization and quantification system described herein may be integrated with the ultrasound imaging apparatus to provide an ultrasound imaging system with the functionality described herein. An example of such ultrasound imaging system will be described further below with reference to FIG. 8.

Figure 2:
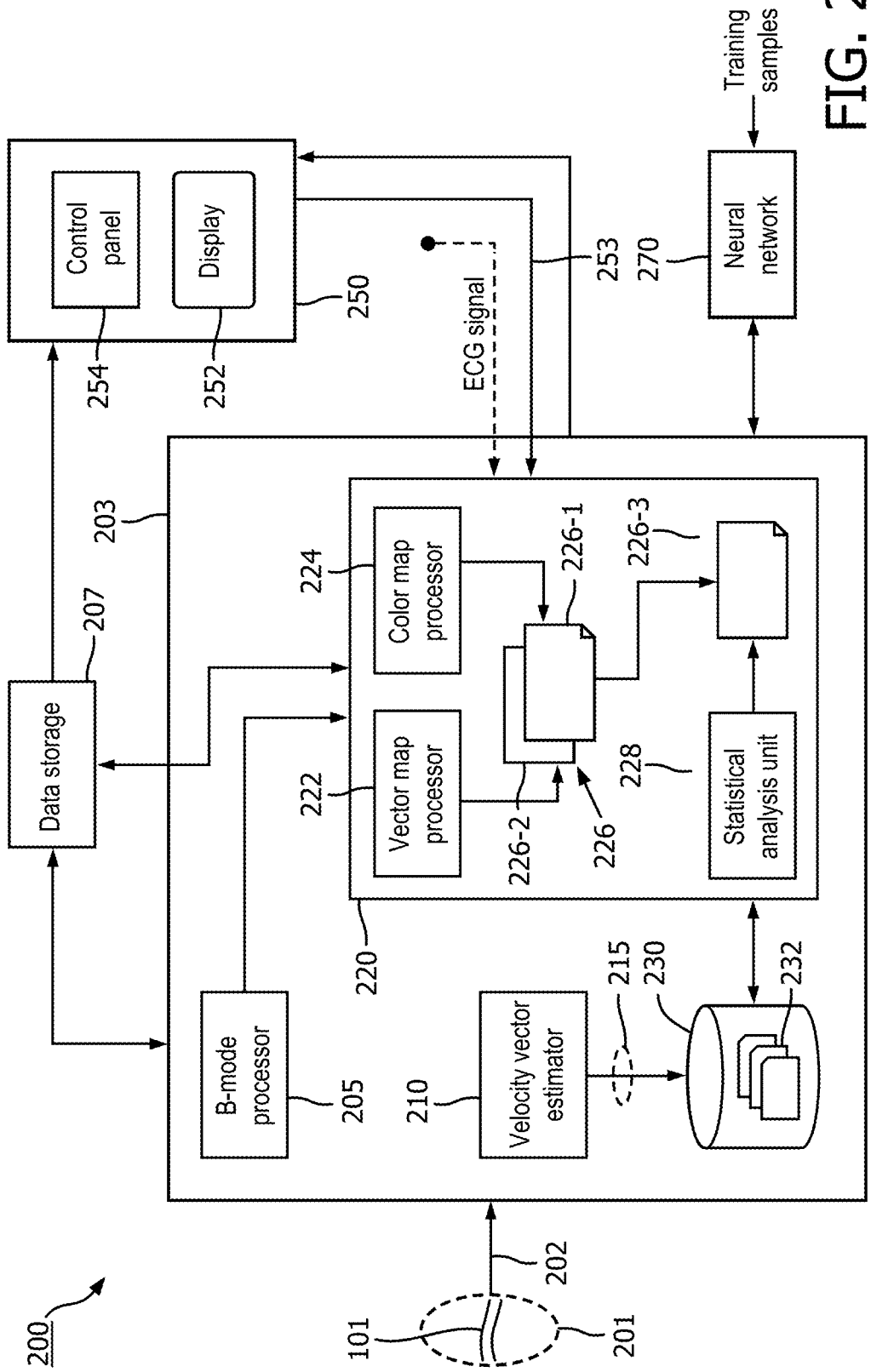
FIG. 2 is another block diagram of a visualization and quantification system in accordance with principles of the present inventions.

FIG. 2 shows a block diagram of components of a system according to embodiments of the present disclosure. The components of system 200 will be described with reference also to FIGS. 3-6, which show user interface windows provided by a system for visualization and quantification according to some examples herein. Multiple examples of screen captures of ultrasound images of a bodily structure are shown in FIGS. 3-6 to aid in better illustrating principles of the present invention. As shown in FIG. 2, system 200 may include a processor 203 and a display unit 252. The processor 203 may be part of an ultrasound imaging system and may include or be communicatively coupled with B-mode processor 205, which is configured to generate B-mode images of a scanned anatomical structures (e.g., a bodily structure 101, such as a blood vessel, and a fluid flowing within the bodily structure).

In accordance with the principles of the present invention, the processor 203 may be configured to generate multi-directional velocity data and enable the user to visualize and quantify aspects of the multi-directional velocity data. To that end the processor 203 may include a velocity vector estimator 210 and a visualization processor 220. The velocity vector estimator 210 may be configured to process received signals (e.g., quadrature or I/Q signals received from a signal processor of an ultrasound imaging apparatus) to estimate the beam-angle-independent velocity of the fluid in any given location within the flow region, interchangeably referred to as vector field data 215. The vector field data 215, in the context of this disclosure may include beam-angle-independent velocity estimates (e.g., axial, lateral and/or elevational velocity components) of the fluid flowing within the bodily structure. The velocity vector estimator 210 may utilize any currently known or later developed technique to obtain the beam-angle-independent velocity data, for example using ultrafast Doppler imaging performed at sufficiently high pulse repetition frequency (PRF) in order to obtain sufficiently high frame rates to enable velocity vector estimation, using the transverse oscillation method or synthetic aperture method (e.g., as described by Jensen et al., in "Recent advances in blood flow vector velocity imaging," 2011 IEEE International Ultrasonics Symposium, pp. 262-271, the disclosure of which is incorporated herein by reference in its entirety for any purpose), or any other vector flow imaging technique.

The velocity vector estimator 210 may output frames 232 of vector field data 215, which may be passed to the visualization processor 220 or temporarily stored in a frame buffer 230, e.g., until accessed by the visualization processor 220 for generating vector field visualization data 226 and/or statistical analysis. For example, vector field data frames 232 may be stored in the buffer 230 until a sufficient number of frames have been obtained for generating time-averaged quantitative displays or histograms. In other examples, the buffer 230 may store frames of visualization data (e.g., frames of vector flow maps or flow direction maps) until they are accessed for concurrent display with corresponding B-mode image frames. The frame buffer 230 may store frames of imaging data used at various stages of the visualization and quantification process, for example, frames of vector field data 215, frames of vector field visualization data (e.g., vector flow maps and/or flow direction maps), as well as quantitiavie information (e.g., histograms or other graphs or plots) of vector flow parameters or various parameters obtained through statistical analysis of the vector flow data, before such data is presented on a display to the user. In some embodiments, the visualization and quantification data may additionally or alternatively be sent to a persistent storage device 207 (e.g., a memory device of a PACS server), where it can be stored for future access. In some embodiments, the processor 203 may additionally or alternatively receive some or all of the ultrasound imaging data needed to generate images according to the present disclosure from the storage device 207. As described, the processor 203 may receive ultrasound imaging data 202 from a ultrasound imaging apparatus in real-time (e.g., while scanning the subject 201 and correspondingly the bodily structure 101), while in other embodiments, the processor 203 may retrieve previously-acquired ultrasound imaging data from the storage device 207 for generating images in accordance with the examples herein.

Figure 3A:
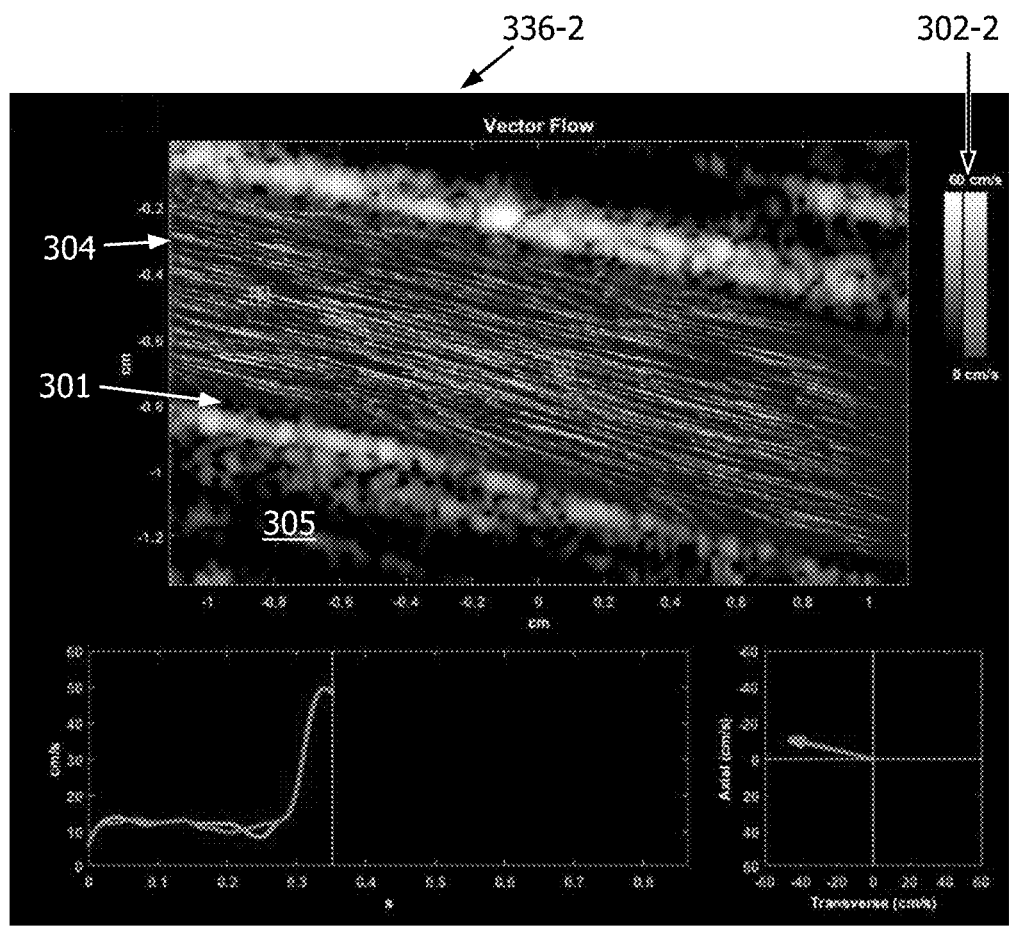
FIGS. 3A and 3B show screen captures of ultrasound images of a bodily structure, specifically flow through a healthy carotid artery, and corresponding velocity vector visualization and flow direction maps in accordance with principles of the present inventions.
Figure 3B:
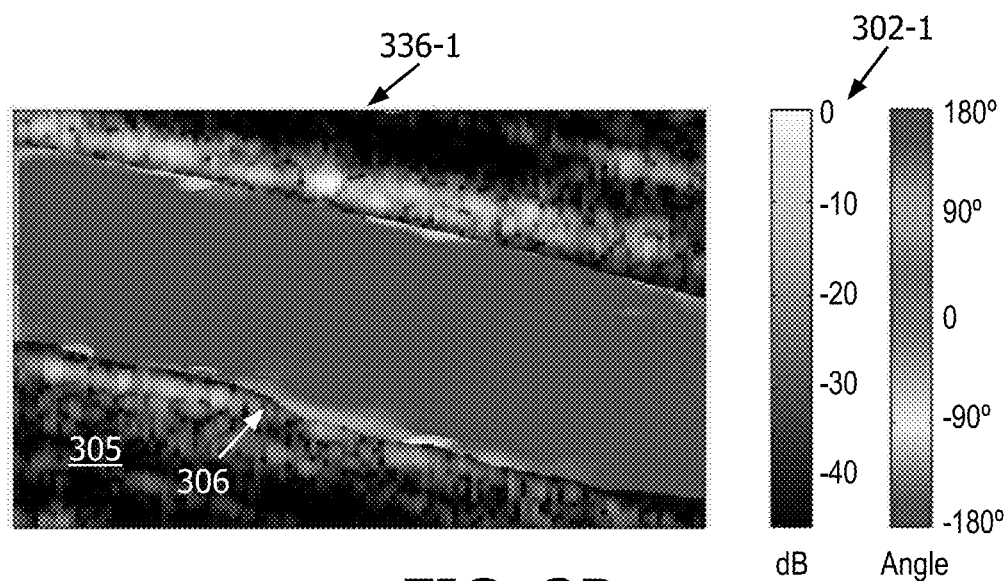
Figure 4A:
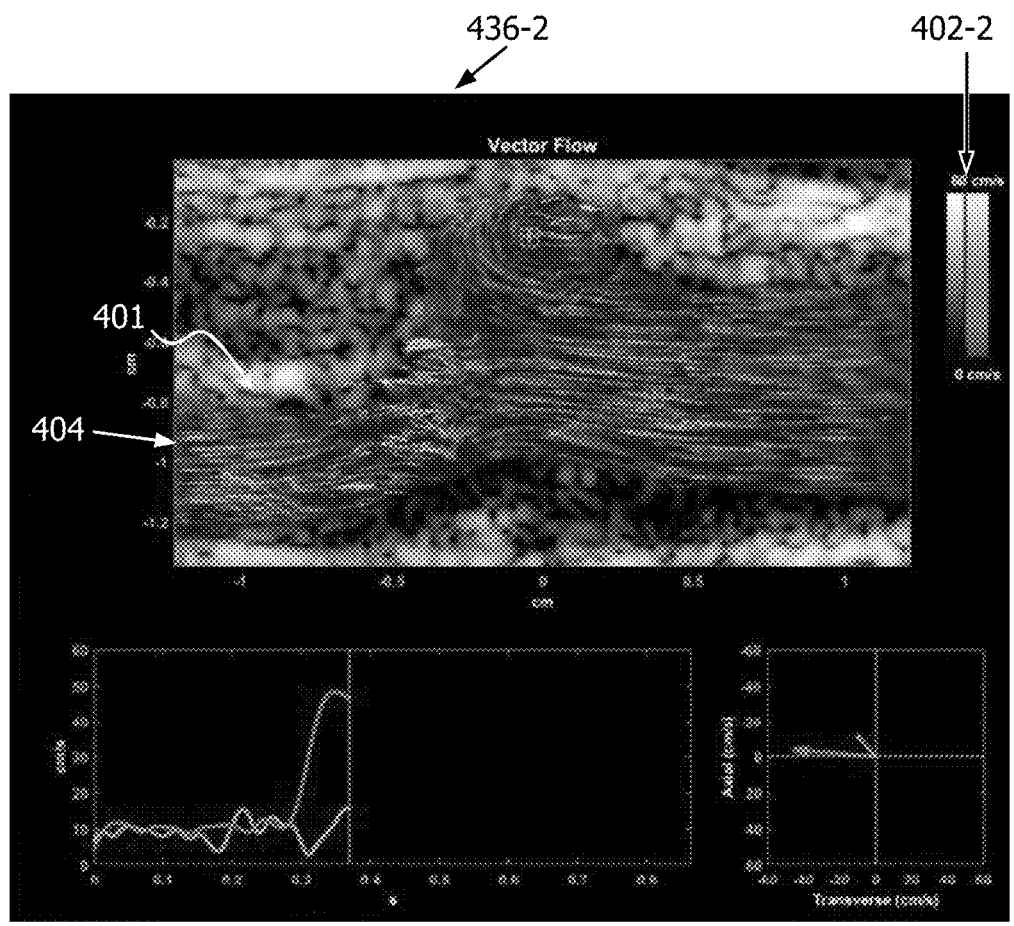
FIGS. 4A and 4B show screen captures of ultrasound images of another bodily structure, in this case flow through a carotid artery with plaque, and corresponding velocity vector visualization and flow direction maps in accordance with principles of the present inventions.
Figure 4B:
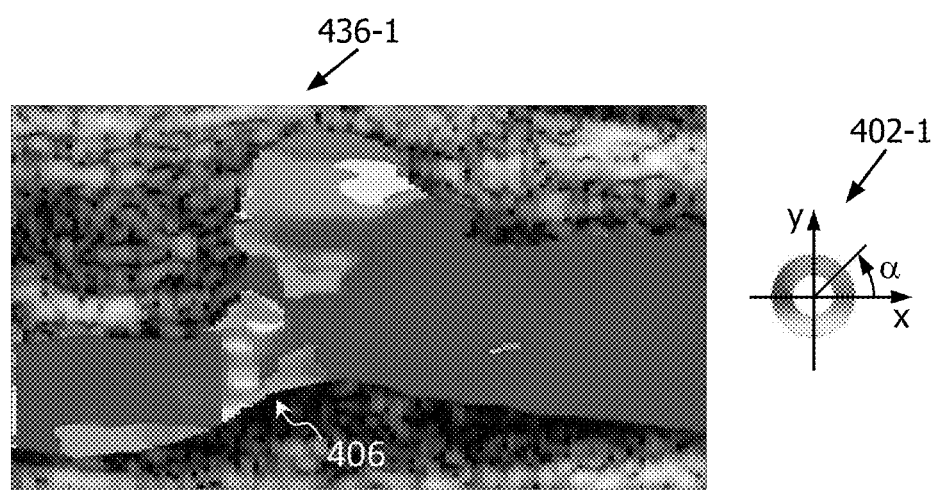
Figure 10:
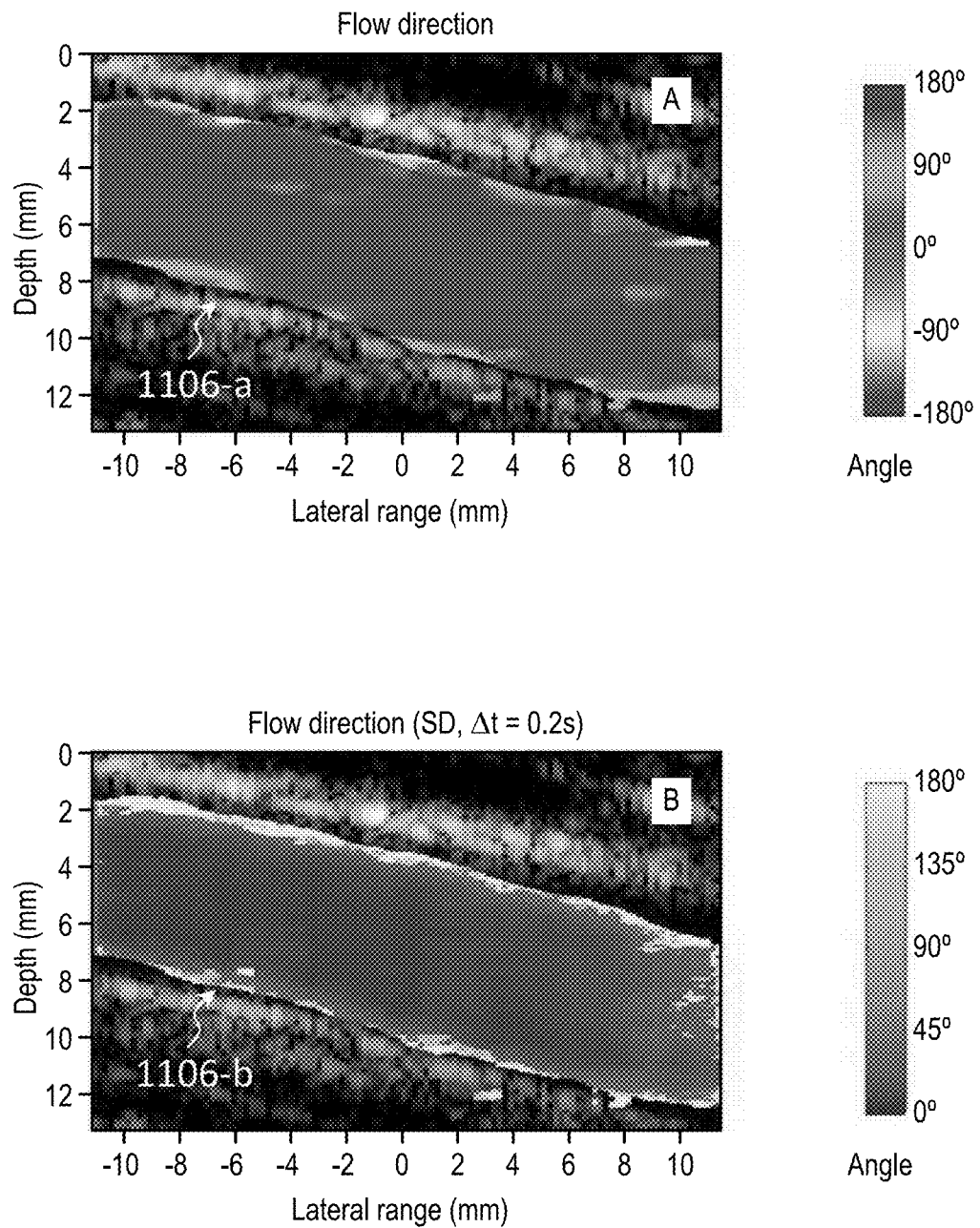
FIG. 10 shows examples of color maps generated using beam-independent velocities of flow in a healthy blood vessel.
Figure 11:
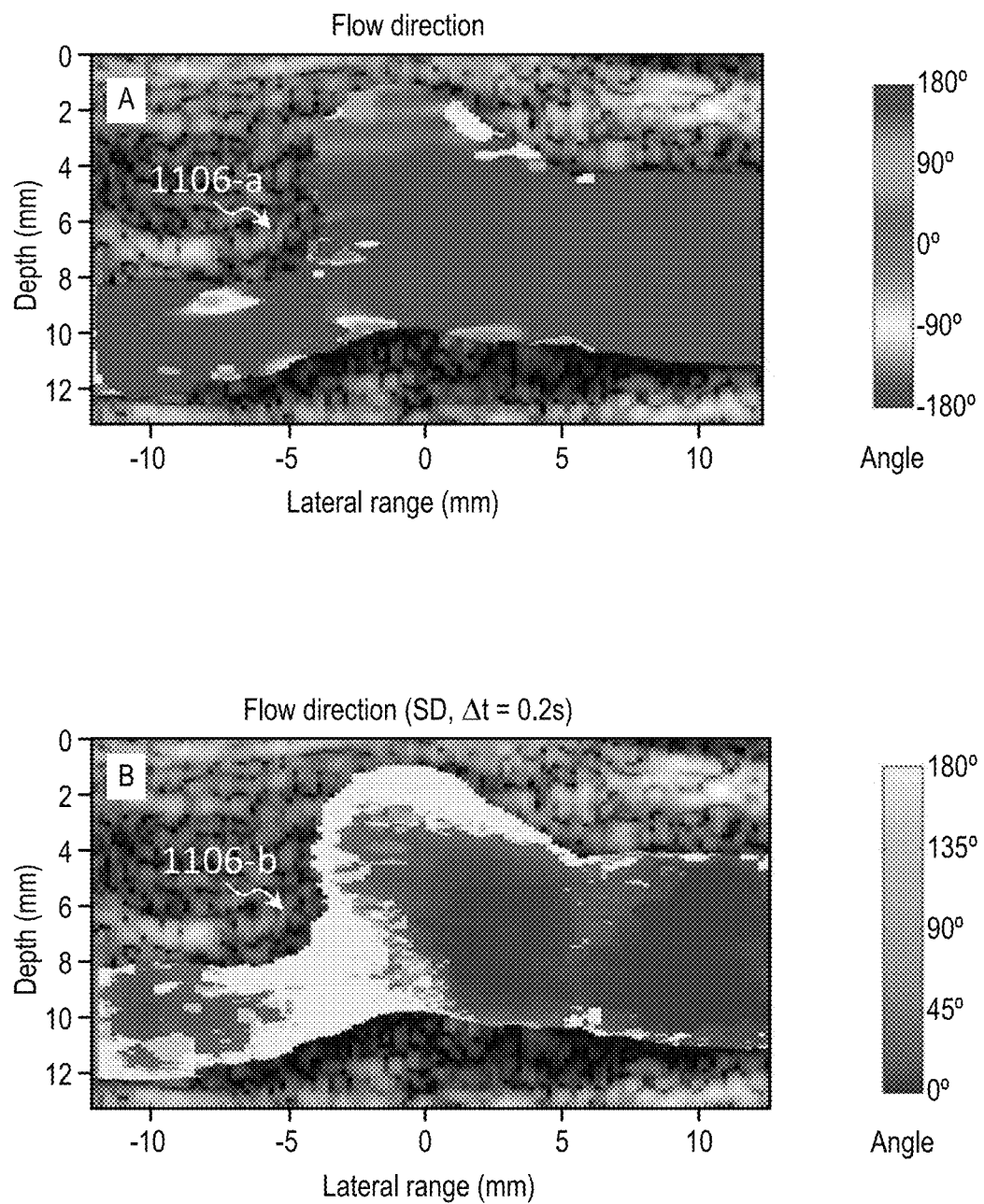
FIG. 11 shows examples of color maps generated using beam-independent velocities of flow in a carotid artery with plaque.

The frames of vector field data may be coupled to a visualization processor 220 which is configured to provide different types of visual and quantitative information (e.g., image frames 226) based on the beam-angle-independent velocity data. The visualization processor 220 may include at least one of a vector map processor 222 and a color map processor 224, which are configured to generate color overlays for visualizing certain aspects of the vector flow data. For example, the vector map processor 222 may generate visual representations of some or all of the velocity vectors associated with the flow region. These visual representations, which may be interchangeably referred to herein as vector flow maps, may be in the form of fixed arrow visualizations, free arrow visualizations, pathlet-based visualizations, e.g., as shown in FIGS. 3A and 4A, or other suitable vector flow imaging visualization technique. The color map processor 224 may generate color maps of a given parameter, for example the flow direction as shown e.g., in FIGS. 3B, 4B, 5 and 6, of the fluid flow at any given location within the flow region. For example, in the case of a flow direction color map, the flow direction at any given location or another flow-related parameter may be encoded in color and presented as a color map, for example as shown in FIGS. 3B and 4B. The flow direction color maps and/or the vector maps may be overlaid with corresponding frames of background B-mode images of the anatomy (e.g., of bodily structure 101) to produce the ultrasound image frames 226-1, 226-2, which may be displayed on display unit 252 in real-time, or stored (e.g., in storage device 207) for later analysis. Multiple temporally sequential image frames may be displayed and/or stored for generating cineloops of vector flow visualization data overlaid on B-mode image data. Thus, in accordance with the examples here, the system 200 may generate one or more ultrasound images 226-2, which include an a vector flow map overlaid on corresponding B-mode images, and may additionally or alternatively generate one or more ultrasound images 226-1, which include a color map of a flow variable (e.g., a flow direction map) overlaid on corresponding B-mode images. In some examples, the color map processor 224 may alternatively or additionally generate color maps of one or more different parameter associated with the flow, for example a statistical variability parameter obtained through statistical analysis based on the velocity vectors, such as a standard deviation of the flow direction, e.g. as shown in FIGS. 10 and 11. For example, as shown in FIGS. 10 and 11, the standard deviation of flow directions, which may be temporally-averaged over a given period of time (e.g., 0.2s) may be calculated on a pixel-by-pixel basis and displayed as a color map 1006-b, 1106-b rather than a histogram as in other examples herein. In each of FIGS. 10 and 11, the upper images (A) show an example of a flow direction color map 1006-a, 1106-a and the lower image (B) shows the corresponding standard deviation of flow directions color map 1006-b and 1006-b associated with the respective flow direction color maps 1006-a and 1106-a. As will be appreciated, a variety of other types of parameters associated with the flow (e.g., other statistical variability parameter such as mean, median, moving average, or others) can thus be presented visually to the user, e.g., to assist with appreciating blood flow hemodynamics and assist with diagnosis.

The visualization processor 220 may further include a statistical analysis unit 228, which is configured to perform statistical analysis on the vector field data 215 to provide additional quantitative information 226-3 about the fluid flow. In some embodiments, statistical analysis may be performed on data associated with a sub-region within the flow region for which vector flow was obtained. The sub-region, also referred to as selected region of interest (ROI), may be user-selected, for example responsive to user inputs 253 via a control panel 254 of user interface 250. In other examples, the selected ROI may be automatically defined by the processor 203, in some cases based on statistical analysis performed broadly over a portion or substantially all of the flow region. For example, the flow in the flow region (e.g., within the vessel) may be analyzed to identify areas of turbulent flow and the region associated with greatest turbulence may be selected as the initial selected ROI. In some examples of the system, the processor may be configured to receive subsequent user input to move and/or resize the processor-selected ROI. In yet further example, the processor may be configured to receive user input to select additional ROIs which may be concurrently analyzed and or visualized with the initially selected ROI. Quantitative information 226-3 may be generated and displayed for one or more ROIs within the flow region, as will be described further with reference to FIGS. 3-6.

The ROI selection may be based on vector flow visualization data provided either by the vector map processor 222 or the color map processor 224. That is, in some examples, the system may display only one type of overlay image and the user may select the ROI on the type of overlay provided. In other embodiments, the system may generate and display, in some cases concurrently, both a color map overlay 226-1 and a vector map overlay 226-2, and the user may select the ROI for quantification on either of the two images. In some examples, statistical analysis may be performed on the same flow parameter which is color coded in the color map overlay 226-1 (e.g., flow direction), such as when the user or the system select the ROI based on a displayed color map overlay image. In other examples, the system may be configured to provide additional user controls (e.g., via the control panel 254) for specifying the flow parameter(s) for statistical analysis. Also, while the control panel 254 and display 252 are illustrated as separate components, it will be understood that in some embodiments, the control panel 254 or at least part of the functionality of the control panel for providing user controls may be integrated into and provided by a touch-sensitive display which also provides the function of displaying the images according to the examples herein.

In some examples, certain functions of the processor 203 may be enhanced by machine learning. For example, processor 203 may be communicatively coupled to a neural network 270 trained to identify a suspicious region from the larger imaged flow region. In such examples, the statistical analysis unit 228 may receive input, such as thresholding parameters for comparison against the one or more measures of variability that may be computed by the statistical analysis unit 228 for identification of the selected ROI. In some examples, the ROI identification may be performed substantially by the neural network, which may be trained to recognize certain flow patterns that may be indicative of vascular occlusions (e.g., vessel stenosis) or other types of vascular disease. The neural network 270 may be trained using training samples (e.g., prior patient screenings) from a diverse set of subjects that capture intra-patient and inter-patient variations, e.g., race, age, gender, etc. and other factors that may affect the suspicious region identification. The trained neural network 270 may then receive information about the subject (e.g., patient) being scanned and may identify or provide thresholds to the statistical analysis unit 228 for identifying a suspicious region for further quantification. Training samples may be retrieved from a data storage device (e.g., data storage 207 or the cloud).

Referring now also to FIGS. 3-6, further examples of visualization and quantification data in accordance with the present disclosure will be described. FIGS. 3A and 3B show screen captures of ultrasound images 336-2, and 332-1, respectively, which show the blood flow through a bodily structure 401, in this case through a healthy carotid artery, at a given instance in time. In the image 336-2 in FIG. 3A, the visualization of the velocity vector data is provided in the form of a vector flow map 304, while in the image 336-1 in FIG. 3B, the visualization is provide in the form of a color map 306. To generate the color map 306 of the example in FIG. 3B, the flow direction at any given location or pixel within the flow region is encoded in color and overlaid for display on a background image 305 of the anatomy. Each type of visualization data is associated and accompanied with a color key (e.g., color keys 302-2 and 302-1 as displayed concurrently with images 336-2 and 336-1, respectively). In the case of the vector flow map where individual paths of tracked fluid particles are visualized using arrows or pathlets (in this case, pathlets), the magnitude of the velocity vectors may be encoded in color, for example by assigning two different colors to the minimum and maximum velocity (e.g., yellow for the minimum velocity magnitude of 0 cm/s and red for the maximum velocity, in this case 60 cm/s) and linearly interpolating a color gradient between the two colors associated with the minimum and maximum velocities and then assigning the corresponding color values to the pathlets in the vector flow map. The color gradient may be displayed as a gradient may be displayed as color key 302-2 alongside image 336-2.

In the case of image 336-1 which is superimposed with a color map 306, the mapped parameter, in this case flow direction, may be encoded using a color key 302-1. In some examples, the color key 302-1 associated with the color map may be defined by assigning at least three primary colors to three distinct flow directions and generating color gradients between each pair of adjacent primary colors to produce a color gradient for the full range of flow directions. The direction of flow at any given location may be defined in terms of the angle between a nominal direction (e.g., a nominal lateral direction going from the left side to the right side of the image) and the velocity vector as defined by the lateral and axial velocity components at that given location. Thus, a velocity vector having only a lateral component and a zero axial component may define a flow direction of either 0 degrees or 180 degrees, depending on whether the velocity vector points towards the left side or right side of the image. In the specific example in FIG. 3B, the color key may be defined using the three primary colors red, blue and yellow. The color red may be assigned to the 0 degree flow direction, that is, in this example a purely lateral velocity vector in a direction from left to right of the image. The color blue may then be assigned to the 180 degree flow direction, that is, in this example to purely lateral velocity vectors oriented in a direction from right to left of the image, and yellow may be assigned to either the +90 or −90 degree direction, which in this example would be a purely axial velocity vector (i.e., having a zero lateral component) indicative of flow in a direction either from bottom to top of the image or from top to bottom of the image, respectively. A color gradient (e.g., by linearly interpolating between the primary colors) may be generated and respective colors assigned to each unique flow direction of the velocity vectors in the flow region in order to generate the color map. While the example in FIG. 3B shows a color map 306 that maps the flow directions at every location in the flow region, in other embodiments of the present invention a different parameter of variability of the vector field may be mapped instead, for example, the velocity magnitude at each pixel, or a statistical measure of variability of the flow direction or the magnitude in every location or pixel. Also, the color key may be visually presented using different form factors. For example, as shown in FIG. 3B, the color key may be in the form of a color bar, which is a familiar form factor that is also typically used to provide the grayscale key of a B-mode image identifying the range of amplitudes in the image.

In other embodiments, the visual representation of the color key may be in the form of a color wheel, as shown in FIG. 4B. Similar to FIGS. 3A and 3B, FIGS. 4A and 4B show screen captures of ultrasound images of a bodily structure, in this case showing a flow through a carotid artery with plaque. Each of the images 436-1 and 436-2 is overlaid with color data to provide a visualization of the velocity vector field. Similar to the examples in FIGS. 3A and 3B, the image 436-1 is superimposed with a color map 406, again illustrating flow direction as the mapped parameter, and image 436-2 is superimposed with a vector flow map 404. The vector flow map is associated with color key 402-2 displayed alongside image 436-2 and the color map 406 is associated with color key 402-2 displayed alongside image 436-1. In this example, the color key is in the form of a color wheel which is associated with an x-y coordinate frame. The positive x-axis of the coordinate frame is aligned with the 0 degrees or nominal flow direction and the positive y-axis aligned with the +90 degree flow direction. The color gradient may be generated as described above, e.g., by interpolating between adjacent primary colors, and in this case the color gradient is superimposed onto the color wheel to provide a visual indication of the colors corresponding with the different flow directions in the color map 406.

While specific examples have been described with reference to color mapping the flow direction of the fluid, it will be appreciated that the color map may be used to visualize any types of variances of the flow. That is, the color map may provide any type of a variance display, for example localized standard deviation or some other statistical measure for each location in the flow region, color coded and overlaid onto an image of the anatomy. Values quantifying the variance of the flow direction, magnitude or combinations thereof may be generated. These variances may be seen as spatial statistical measures. Histograms may then be used to quantitatively display variances of the flow (i.e. measures of diversity of the flow in any given region). Spatially and/or temporally averaged data may be used for generating histograms according to the present examples.

Figure 5A:
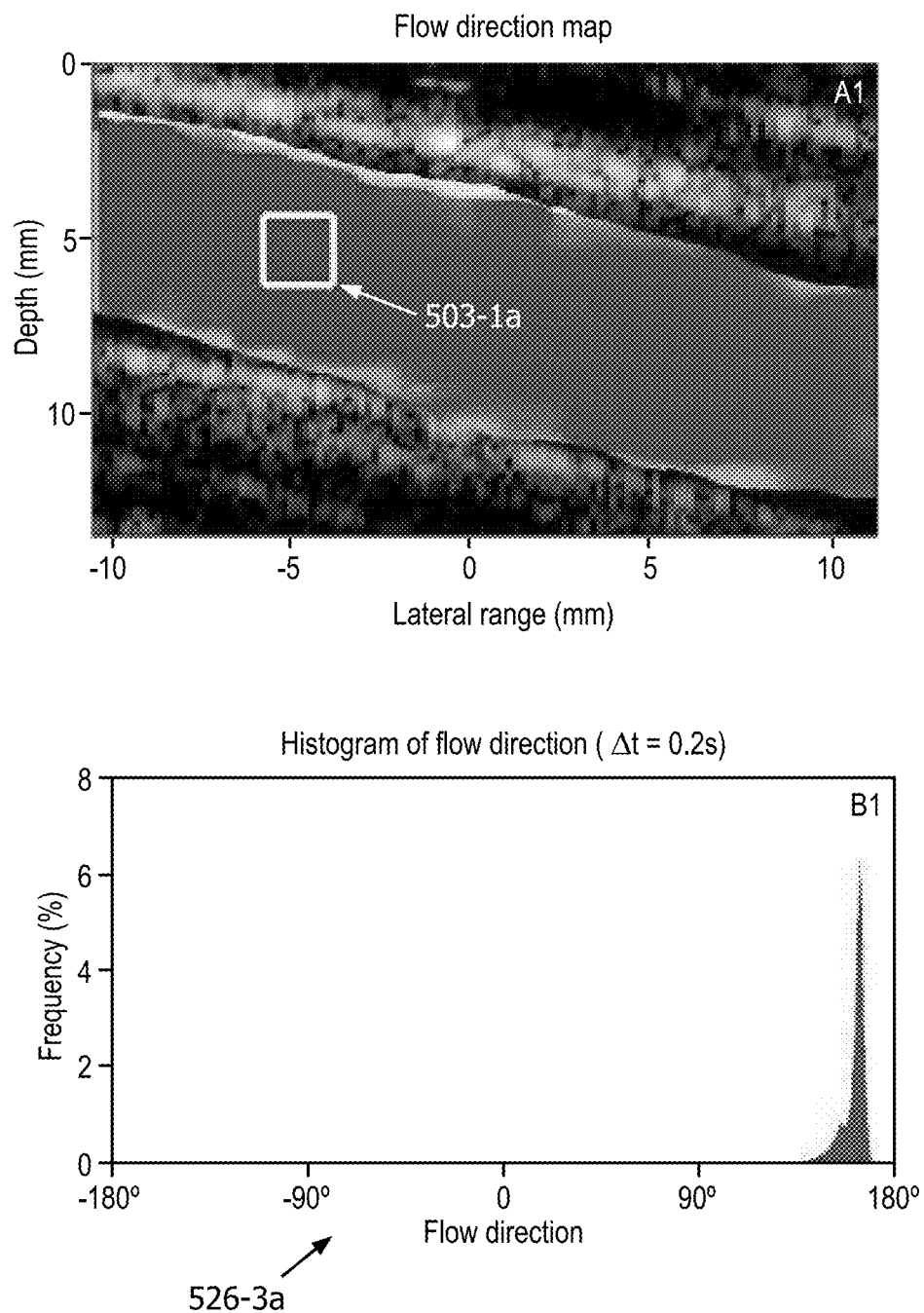
FIGS. 5A and 5B show example histograms at two ROIs associated with the carotid blood flow in FIGS. 3A and 3B.
Figure 5B:
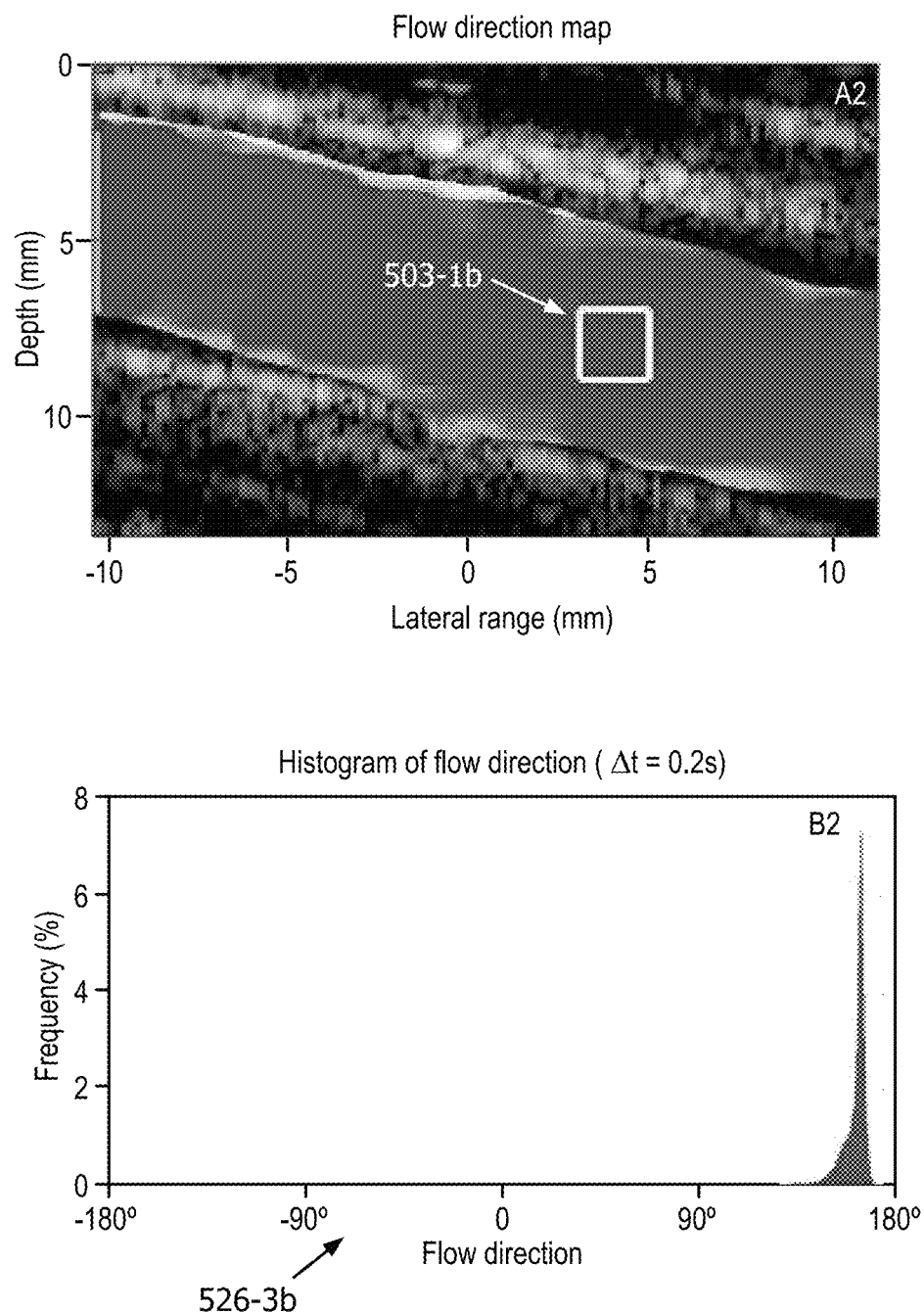
Figure 6A:
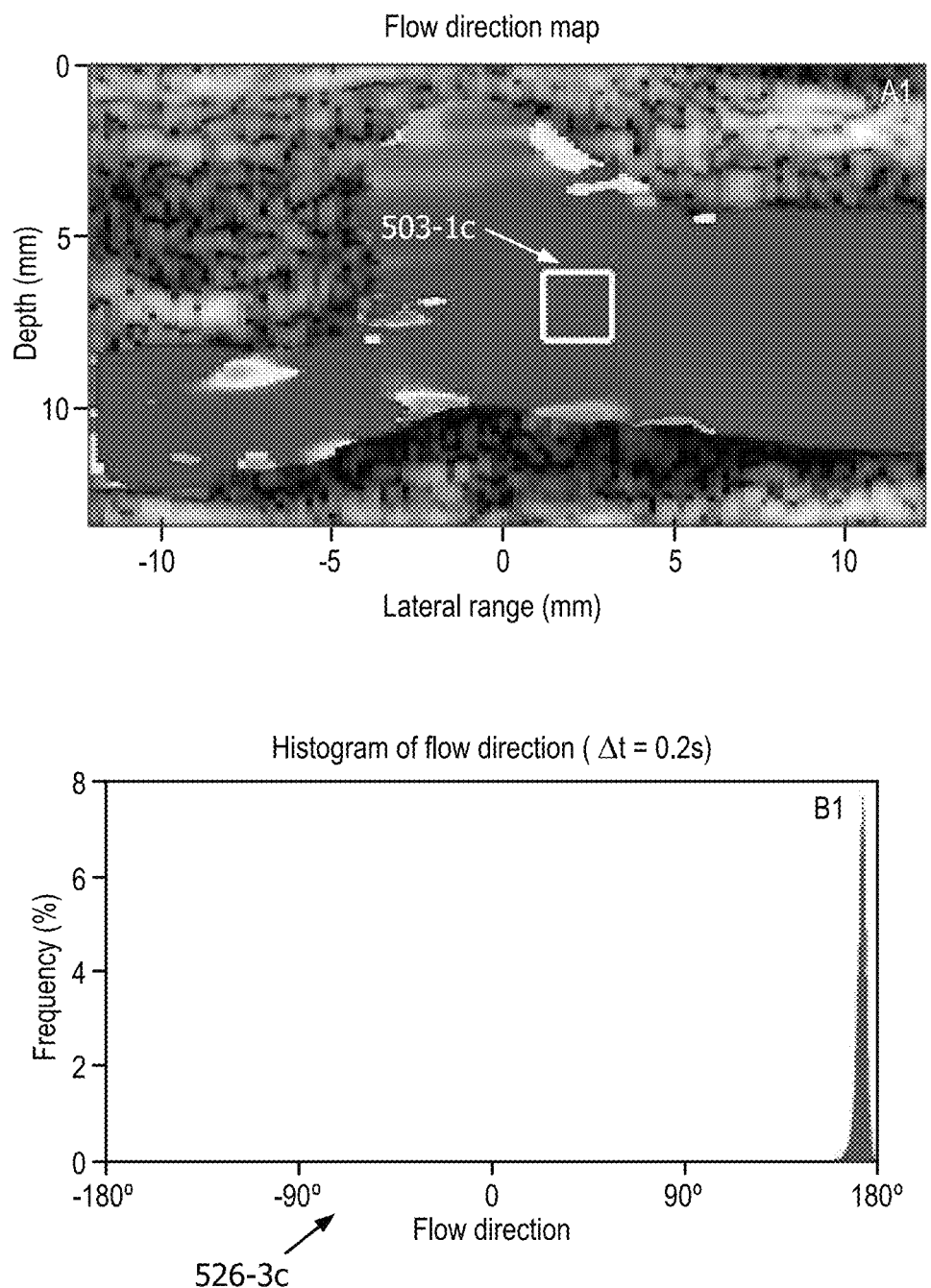
FIGS. 6A and 6B show example histograms at two ROIs associated with the carotid blood flow in FIGS. 4A and 4B.
Figure 6B:
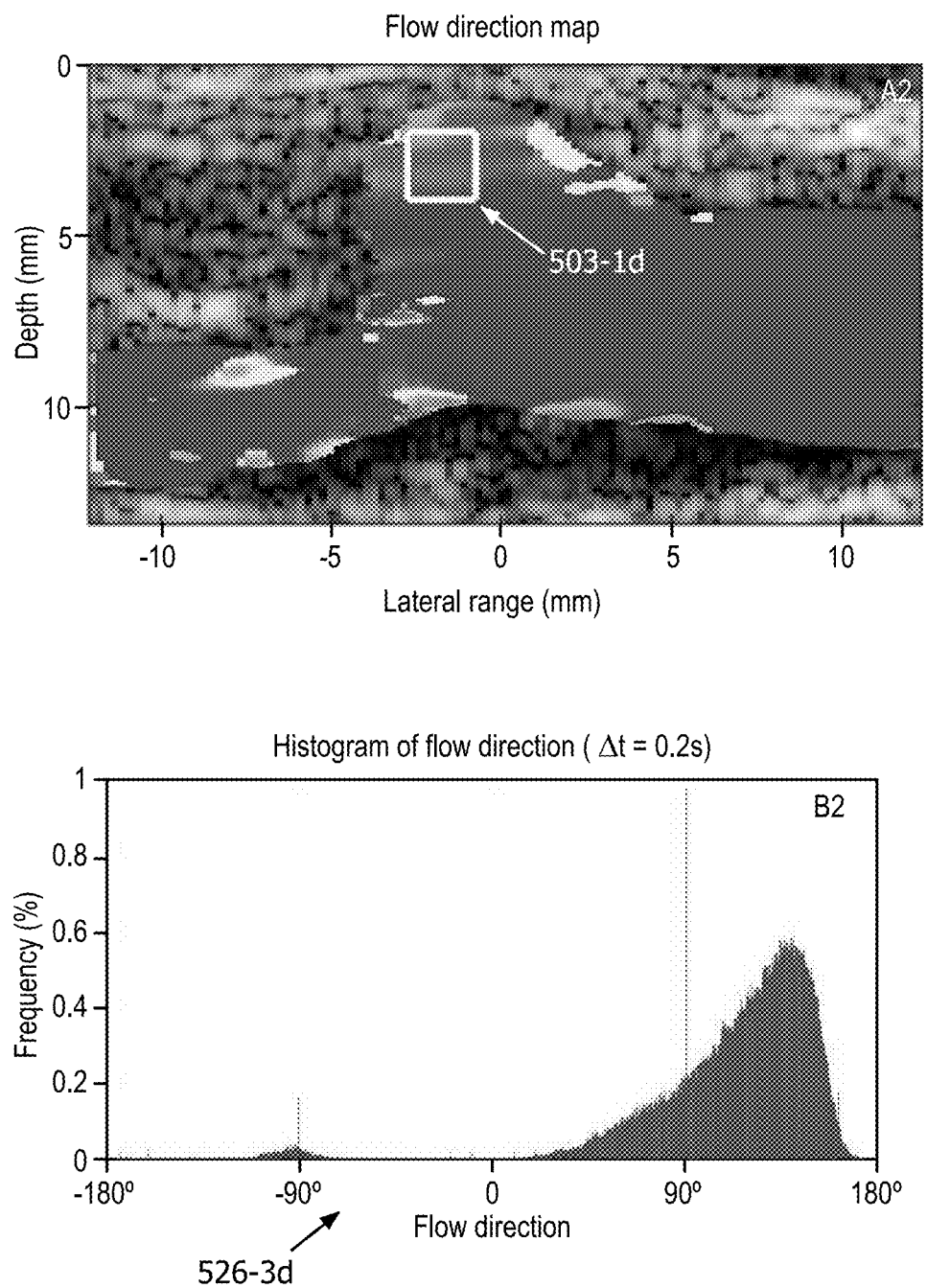

FIGS. 5A and 5B shows example histograms (e.g., 526-3*a* and 526-3*b*) at two selected interrogation regions (or interchangeably, ROIs 503-1a and 503-1b) associated with the carotid flow shown in FIGS. 3A and 3B. FIGS. 6A and 6B shows example histograms (e.g., 526-3c and 526-3d) at two selected interrogation regions (or ROIs 503-1c and 503-1d) associated with the carotid flow shown in FIGS. 4A and 4B. As described, after vector field visualization data has been generated and displayed, an interrogation region or ROI may be selected, for example responsive to user inputs. The user may place a cursor on the vector flow visualization display (e.g., on either of the images 336-1 or 336-2) and outline the ROI by delineating a polygon shape with the cursor (or in the case of a touch sensitive display, may use a finger or stylus to select or outline the ROI on the display). Further quantification would then be performed by the system for the locations (i.e., pixels) in the selected ROI. The system may display the flow distribution in the ROI in the format of histogram of flow direction, speed, or statistical analysis (mean, standard deviation and/or higher order statistics) associated with the flow direction or speed. In yet further examples, combination of parameters may be displayed using 2D histograms (e.g., as shown in FIGS. 6C and 6D).

The system may generate the flow direction histogram of the selected ROI over a small period of time (a fraction of a cardiac cycle). As such, the flow direction values displayed in the histograms in the examples in FIGS. 5-6 are based on temporally-averaged vector flow data (in the illustrated examples, averaged over a period of 0.2 seconds around systole). The time period for temporal averaging may be user-specified or pre-programmed, and in some examples, it may be additionally and optionally defined using an ECG signal. The histogram may be static or dynamically updated in real-time. In some examples, the histograms may be retrospectively generated from a cine loop, for example when an imaging system is in freeze mode. As shown in FIGS. 5A and 5B, the flow through a healthy carotid may be generally laminar thus resulting in a narrow-band histogram centered around the predominant direction of the flow. Both ROIs 503-1a and 503-1b produce similarly narrow-band histograms indicative of healthy laminar flow. The relatively narrow or tight distribution of the flow direction in the two selected regions 503-1a and 503-1b are indicative of a healthy fully opened lumen with a uniform cross-section. In contrast, in the examples in FIGS. 6A-6D, the histograms of the second selected region 503-1d show a wider distribution of flow directions and thus is indicative of greater variance and thus more turbulent flow, which may indicate a vessel occlusion such as plaque buildup or other reason for the flow disturbance that may indicate vessel disease.

Figure 6C:
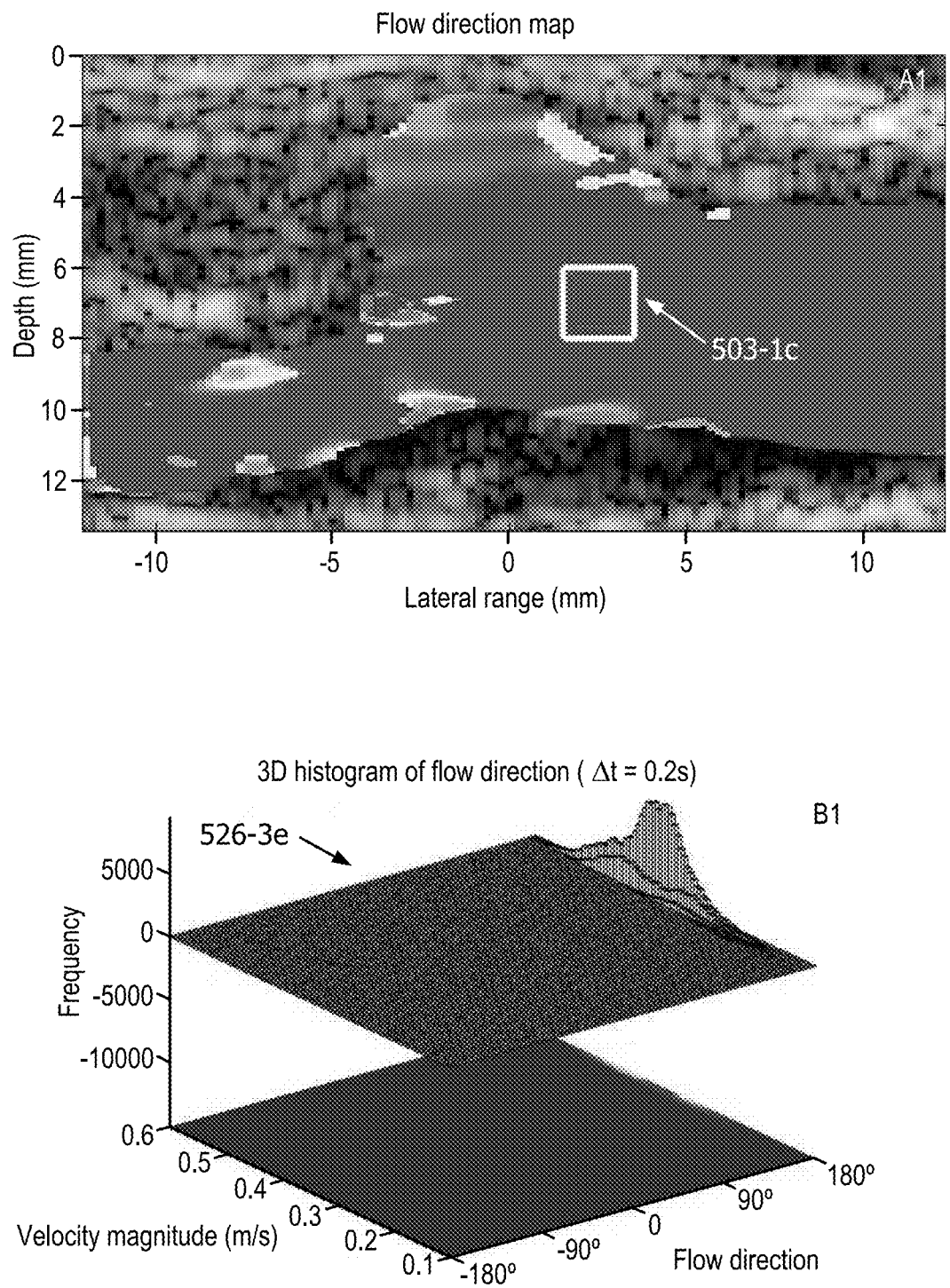
FIGS. 6C and 6D show example 2D histograms at two ROIs associated with the carotid blood flow in FIGS. 4A and 4B.
Figure 6D:
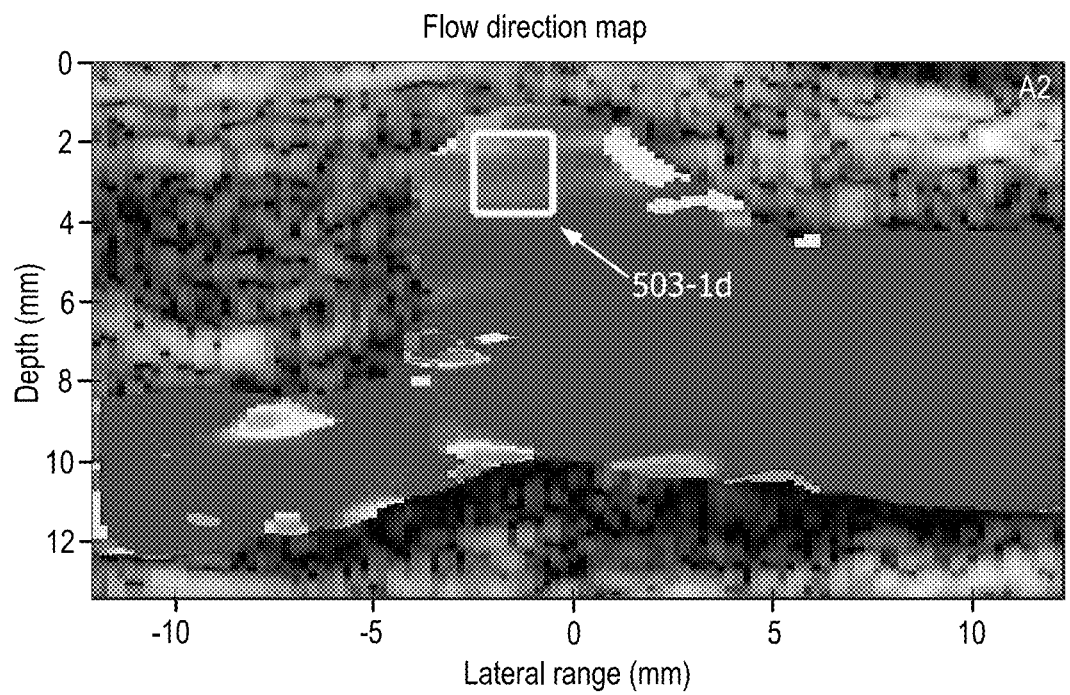
Figure 6D:
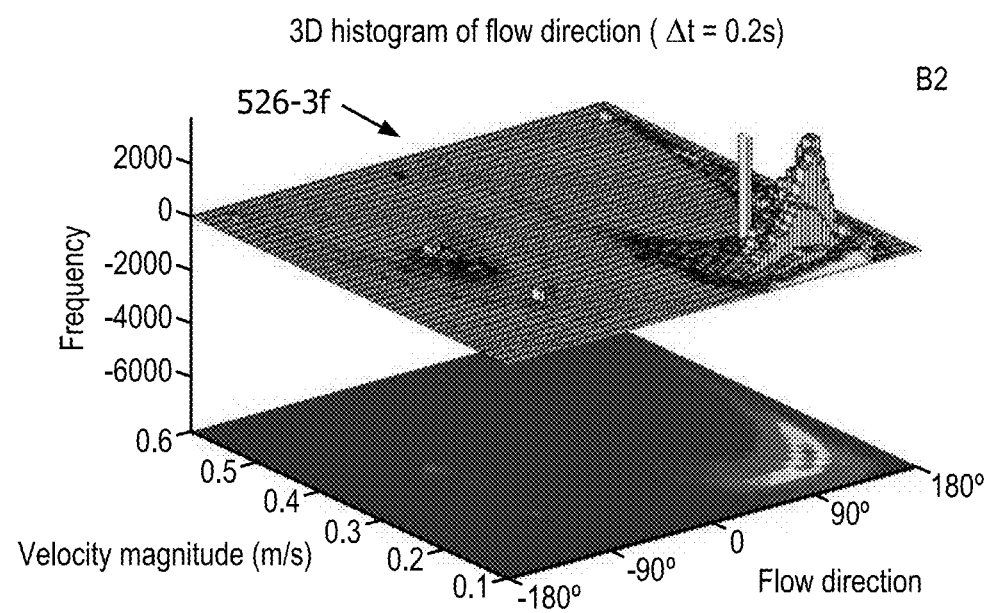

In other examples, 2D histograms (e.g., 526-3e and 526-3f), which simultaneously plot multiple parameters and are presented for example in 3D fashion as shown in FIGS. 6C and 6D, may be generated. In the specific illustrated example, both flow direction and flow speed are displayed in the histograms 526-3e and 526-3f associated with the same two regions 503-1c and 503-1d, respectively that were shown also in FIGS. 6A and 6B. As can be observed from the histogram 526-3e, the first region (503-1c) exhibits a relatively uniform or narrow distribution of flow directions across the ROI and a generally bell-shaped distribution of the velocity magnitudes across the ROI as is typical since steady flow through a lumen tends to have higher velocities in the center and lower velocities towards the walls of the lumen. In contrast, the second region (503-1d) exhibits a less uniform or wider distribution of flow directions across the ROI and also a less regularly shaped distribution in the velocity dimension. As such, the 2D histograms may reveal additional quantitative information that may help physicians make better decisions.

As described, the ROI may in some cases be system-selected, such as based on statistical analysis. For example, the system may initially perform statistical analysis over the broader flow region to identify sub-regions having flow variability. Once identified, a visual indicator of the system-selected ROI (also referred to as measurement or statistical analysis box) may be provided on the image and the velocity information (e.g., flow direction, magnitude, or combinations thereof) and/or statistical data associated with the pixels within the ROI may be formatted for display (e.g., presented in histograms as described herein). In some cases, the system may be configured to enable the user to re-size and/or move the statistical analysis box to display quantitative and/or statistical information about other portions of the flow region. When generating displays in real-time, such as visualization of the vector field data and color maps, the various displays may be synchronized and displayed with the same refresh rate.

As described, vector flow maps according to the present disclosure may be generated using pathlet-based visualization techniques, for example by generating and dynamically updating a visual representation of the frontal portion of the path traveled by the tracked particles. In this manner, e.g., by dynamically updating the pathlets (e.g., in real time or retrospectively as part of a cineloop visualization), the vector flow image may provide a visual cue of the movement of the tracked particles (e.g., blood flow). Each pathlet begins fading out when a distance from the tip exceeds a given threshold. That is, a head of the pathlet is always more opaque than the tail, enabling easier identification of the moving direction (i.e., flow direction) of the pathlet, even in a static image, without the inclusion of arrows that may clutter the display. Additionally, the pathlets may be color-coded and/or the pathlet length may be proportional to the velocity magnitude, both of these features helping the user more easily visualize the velocity magnitudes.

Figure 7:
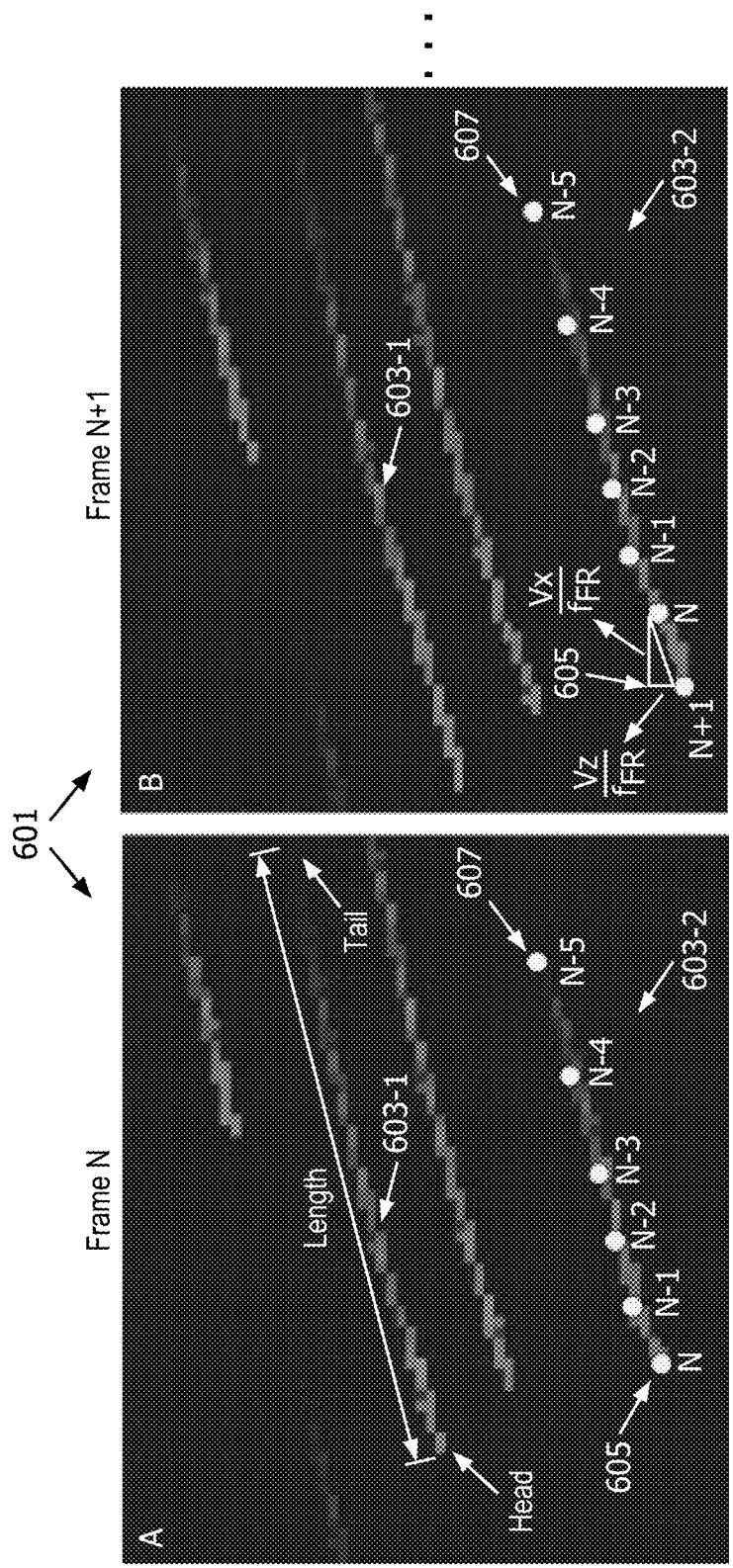
FIG. 7 shows an illustration of a portion of two consecutive frames of ultrasound image data and a technique for updating the pathlet-based information in the frames, e.g., for providing vector flow visualization in accordance with the principles of the present invention.

FIG. 7 shows partial magnified images of two consecutive frames 601 (i.e., frames N and N+1) of a pathlet-based vector flow map, which includes pathlets 603-1 and 603-2. The pathlets in the vector flow map, as well as the vector flow map generally, may be defined using several parameters, including length (alternatively, or additional and optionally, duration), width, and density of pathlets, generation rate of new pathlets (or alternatively vanish rate of old pathlets), color range for mapping of pathlets, display frame rate, and transparency and color of the flow mask, any of which parameters may be user-configurable (before or during imaging) to obtain a desired visualization effect without compromising the diagnostic performance of the system.

To generate the pathlets, initially a number of frames of the vector field data are saved and pathlets are generated for each frame, for example by interpolating the trajectory of tracked particles over the number of initial frames. For each subsequent frame, the pathelts are updated based on the velocity vector data associated with the subsequent frames. For example, in FIGS. 6A and 6B, the pathlets 603-1 and 603-2 illustrate the frontal portion of the trajectories of two tracked flow particles, the last several locations of one of which are shown by the points N+1, N, N−1, N−2, N−3, N−4, and N−5 which for illustration are so labeled to indicate the frame with which they are associated. The front most point in each frame indicates the estimated location of the tracked particle in that frame. The front most point of the pathlet in each frame (e.g., point N in frame N and point N+1 in frame N+1) is referred to as the head 605 of the pathlet. The pathlets may be updated every frame to reflect the movement of the particle to a new location and thus this movement may be visualized on the display by the changing location of the head 605 of the pathlet in each updated frame. The new location of the tracked particle and thus the head 605 is calculated using the beam-angle-independent velocity estimates (i.e., the axial and lateral velocity components in the case of a 2D map or the axial, lateral and elevational velocity components in the case of a 3D map), which can be obtained in real-time or prior to the visualization. For example the axial displacement of the tracked particle may be calculated as $Vz/f_{FR}$ and the lateral displacement of the tracked particle may be calculated as $Vx/f_{FR}$, where Vx is the lateral velocity (m/s), Vz is the axial velocity (m/s) of the head, and f FR is the tracking frame rate (Hz). A continuous and smooth pathlet is generated by interpolation (linear or cubic) of these discrete dots, and then displayed as an aliasing-free line.

Overtime, the aft end of a particle's trajectory fades, e.g., to reduce clutter on the display, and only the frontal portion of the trajectory is shown on the display. The aft end of the displayed pathlet is referred to as the tail 607 of the pathlet. The pathlets (e.g., pathlets 603-1 and 603-2) may be color-coded based on the velocity magnitude at different locations (i.e., each segment 609 between the location of the particle in a previous frame and the location of the particle in the he current frame may reflect the estimated velocity magnitude of the particle in the current frame). A color key for the vector flow map (e.g., keys 306-2 or 406-2 associated with the vector flow maps in FIGS. 3A and 4A, respectively) may be displayed concurrently with the vector flow image. In addition to color-coding, the transparency of each pathlet may be linearly distributed with the highest opacity at the head 605 and decreasing to lowest opacity at the tail 607. The transparency distribution may also be updated at each frame. That is, when a new segment 609 is added in a new frame, the transparency may be linearly re-distributed with highest opacity (e.g., 50% or other) at the head 605 and decreasing to e.g., 100% transparency at the tail 607. The transparency may be linearly distributed, such as on a per pixel basis along the length of the pathlet or on a per segment basis. In this manner, the transparency distribution of the pathless may enhance the ease in identifying the direction of flow, even in a static image.

As previously described, each pathlet may have a maximum length, which may be pre-set or user defined. As the pathlet is update frame to frame, it grows in length in each frame due to the addition of a new segment at the head while maintaining the same tail. Once the pathlet reaches its maximum length (e.g., after being updated certain number of frames), it maintains a length shorter than the maximum length by deletion of the oldest location of the particle and correspondingly the aft most segment (also referred to as tail segment). If the pathlet is further defined by duration, with each frame in which the pathlet is updated, a lifetime variable of the pathlet is incremented until the lifetime variable of a given pathlet reaches the maximum lifetime, at which point the pathlet is removed from the display. For example, alternatively or additionally, each pathlet may have a lifetime, which can be defined using an integer variable randomly generated between the maximum pathlet length and the maximum lifetime when the pathlet is created. The age of a pathlet is decrease by one for each frame (e.g., every time the pathlet is updated). Once the age reaches zero, the pathlet is deleted from the vector flow map. A new pathlet may be created at the same time or in a different frame with another random lifetime assigned to it. With this lifetime feature, a balanced spatial distribution of pathlets may be maintained. The pathlets may be updated using an iterative process for any subsequent frame.

When the inputs (e.g., array variables including lateral position (x), axial position (z), lateral velocity Vx, and axial velocity (Vz), and two integer variables including "head of pathlet", and "lifetime of the pathlet") are received by the vector flow processor, the locations and lifetimes of the pathlets are examined. If a pathlet is located within the flow region, and its lifetime is greater than zero, it is defined as an active pathlet. If the pathlet moves outside of the flow region, or its lifetime is zero, it is defined as an inactive pathlet. For any active pathlets, the new head is computed based on the velocity maps, and the lifetime decreased by one. Any inactive pathlets are deleted from the display. An inactive pathlet may be replaced with a new pathlet for example, by randomly generating a new location and a new lifetime for the replacement pathlet. After the data structure for each pathlet is updated, the vector flow processor may generate (e.g., by interpolation) a smooth and continuous aliasing-free line to visualize the pathlets. The color of the line corresponding to each pathlet is coded based on the velocity magnitudes and the transparency of the color-coded pathlet is distributed along its length (i.e., from the new head to new tail of the pathlet) for rendering on the display.

Figure 8:
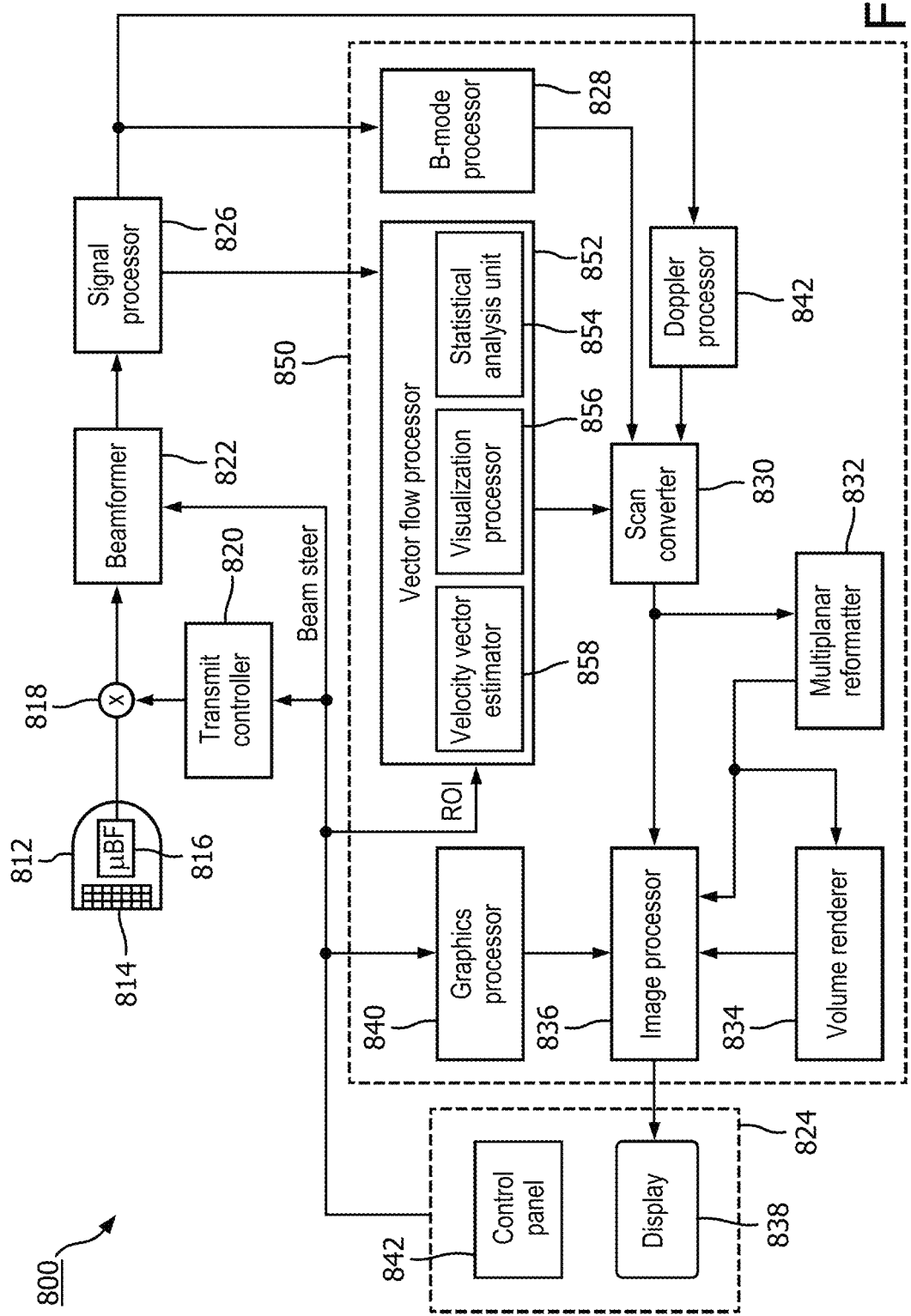
FIG. 8 shows a block diagram of an ultrasound imaging system in accordance with further examples of the present disclosure.

FIG. 8 shows a block diagram of an ultrasound system 800 according to the present disclosure Some or all of the components of system 800 may be used to implement components of any one of the visualization and quantification systems described herein, for example the ultrasound imaging apparatus of FIG. 1. In some embodiments, the system 800 may include a processor (e.g., processor 850) and a display unit (e.g., display 838) in accordance with any of the examples described herein, for example as described with reference to FIG. 2. The ultrasound system 800 may include an ultrasound transducer array. In the illustrated example, the ultrasound transducer array 814 is provided in a probe 812. In some examples, the array 814 may be implemented using a plurality of patches, each comprising a sub-array of transducer elements and the array 814 may be configured to be conformably placed against the subject to be imaged. The array 814 is operable to transmit ultrasound toward a region of interest and to receive echoes for imaging the region of interest (ROI). A variety of transducer arrays may be used, e.g., linear arrays, curved arrays, or phased arrays. The array 814 may include, for example, a two dimensional array of transducer elements capable of scanning in both elevation and azimuth dimensions for 2D and/or 3D imaging.

The array 814 may be coupled to a microbeamformer, which may be located in the probe or in an ultrasound system base (e.g., in a cart-based system such as the SPARQ or EPIQ ultrasound system provided by Philips. The microbeamformer may control the transmission and reception of signals by the array. The array 814 may be coupled to the ultrasound system base via the microbeamformer 816, which may be coupled (via a wired or wireless connection) to a transmit/receive (T/R) switch 818 typically located in the base. The T/R switch 818 may be configured to switch between transmission and reception, e.g., to protect the main beamformer 822 from high energy transmit signals. In some embodiments, the functionality of the T/R switch 818 and other elements in the system may be incorporated within the probe, such as a probe operable to couple to a portable system, such as the LUMIFY system provided by PHILIPS.

The probe 812 may be communicatively coupled to the base using a wired or wireless connection.

The transmission of ultrasonic pulses from the array 814 may be directed by the transmit controller 820 coupled to the T/R switch 818 and the beamformer 822, which may receive input from the user's operation of a user interface 824. The user interface 824 may include one or more input devices such as a control panel 842, which may include one or more mechanical controls (e.g., buttons, encoders, etc.), touch sensitive controls (e.g., a trackpad, a touchscreen, or the like), and other known input devices. Another function which may be controlled by the transmit controller 820 is the direction in which beams are steered. Beams may be steered straight ahead from (orthogonal to) the transmission side of the array 814, or at different angles for a wider field of view. The beamformer 822 may combine partially beamformed signals from groups of transducer elements of the individual patches into a fully beamformed signal. The beamformed signals may be coupled to a signal processor 826. The system 800 may include one or more processors (e.g., data and image processing components collectively referred to as processor 850) for generating ultrasound image data responsive to the echoes detected by the array 814, which may be provided in a system base. The processor 850 may be implemented in software and hardware components including one or more CPUs, GPUs, and/or ASICs specially configured to perform the functions described herein for generating ultrasound images and providing a user interface for display of the ultrasound images.

For example, the system 800 may include a signal processor 826 which is configured to process the received echo signals in various ways, such as by bandpass filtering, decimation, I and Q component separation, and harmonic signal separation. The signal processor 826 may also perform additional signal enhancement such as speckle reduction, signal compounding, and noise elimination. The processed signals may be coupled to a B-mode processor 828 for producing B-mode image data. The B-mode processor can employ amplitude detection for the imaging of structures in the body. The signals produced by the B-mode processor 828 may be coupled to a scan converter 830 and a multiplanar reformatter 832. The scan converter 830 may be configured to arrange the echo signals in the spatial relationship from which they were received in a desired image format. For instance, the scan converter 830 may arrange the echo signal into a two dimensional (2D) sector-shaped format, or a pyramidal or otherwise shaped three dimensional (3D) format. The multiplanar reformatter 832 can convert echoes which are received from points in a common plane in a volumetric region of the body into an ultrasonic image (e.g., a B-mode image) of that plane, for example as described in U.S. Pat. No. 6,443,896 (Detmer). A volume renderer 834 may generate an image of the 3D dataset as viewed from a given reference point, e.g., as described in U.S. Pat. No. 6,530,885 (Entrekin et al.).

Additionally or optionally, signals from the signal processor 826 may be coupled to a Doppler processor 842, which may be configured to estimate the Doppler shift and generate Doppler image data. The Doppler image data may include colorflow data which may be overlaid with B-mode (or grayscale) image data for displaying a conventional duplex B-mode/Doppler image. In some examples, the Doppler processor 842 may include a Doppler estimator such as an auto-correlator, in which velocity (Doppler frequency) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators. In some examples, the velocity and power estimates may undergo threshold detection to reduce noise, as well as segmentation and post-processing such as filling and smoothing. The velocity and power estimates may then be mapped to a desired range of display colors in accordance with a color map. The color data, also referred to as Doppler image data, may then be coupled the scan converter 830 where the Doppler image data is converted to the desired image format and overlaid on the B-mode image of the tissue structure containing the blood flow to form a color Doppler image.

In accordance with the principles of the present disclosure, the system 800 may include vector flow processing components (e.g., vector flow processor 852), which may be configured to perform the signal and image processing steps for quantifying and visualizing image data as described herein. For example, the vector flow processor 852 may include a velocity vector estimator 858 and a visualization processor 856. The velocity vector estimator 858 may receive signals from the signal processor 826 and perform velocity estimation to obtain the beam-angle-independent velocity vector data, as described herein. The velocity vector data (e.g., vector flow field) may be passed to a visualization processor 856 for generating graphical representations of the velocity vector field data (e.g., vector flow maps, color maps). The vector flow processor 852 may also include a statistical analysis unit 854, which may perform statistical analysis using the vector field data to generate additional quantitative information about ROIs within the imaged tissue. For example, the statistical analysis unit 854 may be operable to determine and display measures of flow variability within the ROI. Images output at this stage may be coupled to an image processor 836 for further enhancement, buffering and temporary storage before being displayed on an image display 854. The system may include a graphics processor 840, which may generate graphic overlays for display with the images. These graphic overlays may contain, e.g., standard identifying information such as patient name, date and time of the image, imaging parameters, and other annotations. For these purposes, the graphics processor may be configured to receive input from the user interface 824, such as a typed patient name. Although shown as separate components, the functionality of any of the processors herein (e.g., the velocity vector estimator 854 and/or the visualization processor 856) may be incorporated into other processors (e.g., image processor 836 or volume renderer 834) resulting in a single or fewer number of discrete processing units. Furthermore, while processing of the echo signals, e.g., for purposes of generating B-mode images or Doppler images are discussed with reference to a B-mode processor and a Doppler processor, it will be understood that the functions of these processors may be integrated into a single processor, which may be combined with the functionality of the vector flow processing components.

Figure 9:
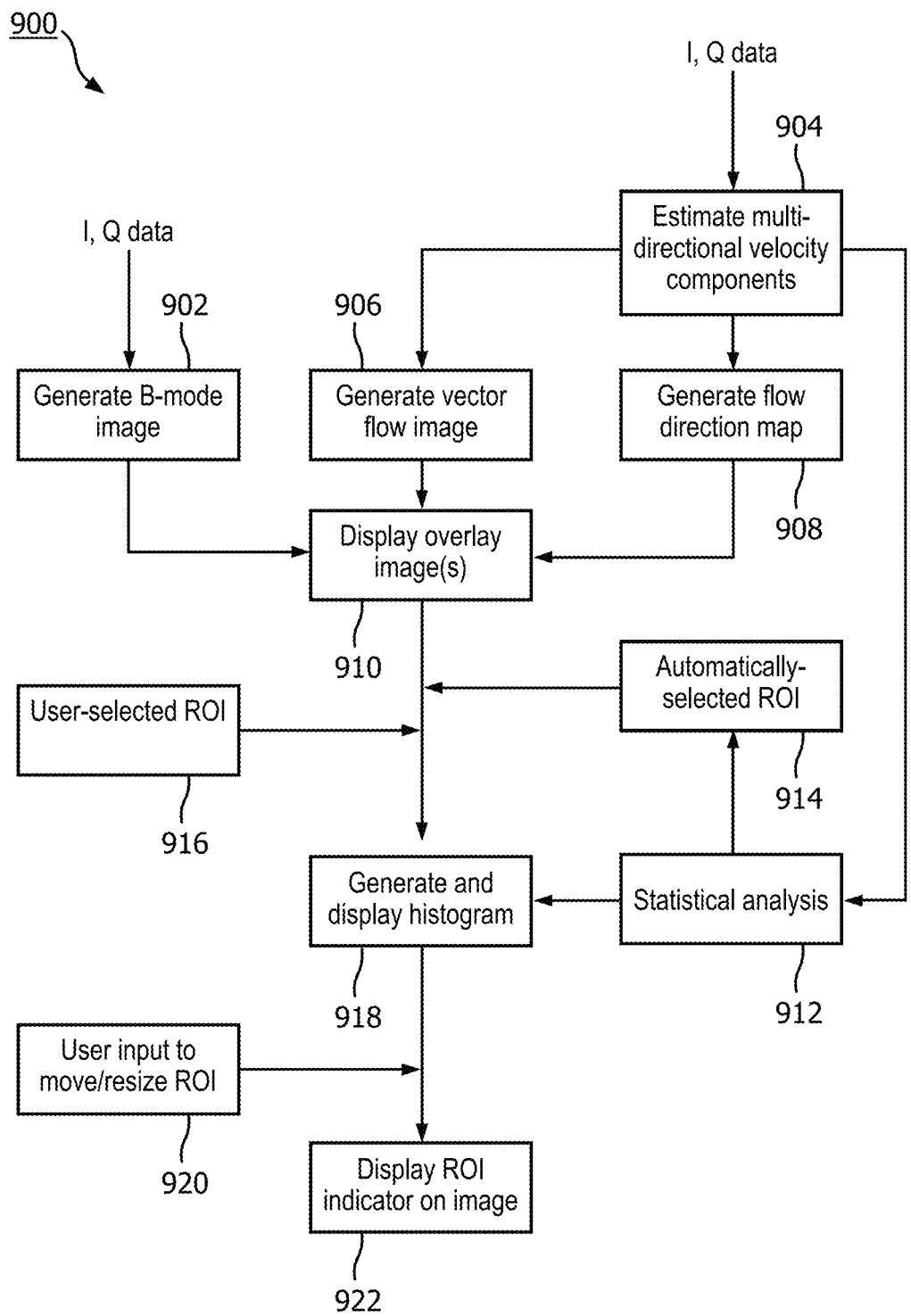
FIG. 9 shows a flow diagram of a process in accordance with examples of the present disclosure.

FIG. 9 shows a flow diagram of a process 900 for visualizing and quantifying ultrasound imaging data in accordance with some embodiments of the present disclosure. The process 900 may be performed by a system (e.g., an ultrasound imaging system, analysis and visualization workstation, etc.) built in accordance with the principles of the present invention and as described further below, for example with reference to FIGS. 1-8. Initially, ultrasound imaging data is acquired such as by scanning with an ultrasound imaging apparatus a subject and more specifically a bodily structure of the subject that contains a fluid throwing therethrough (e.g., a blood vessel). The ultrasound imaging apparatus is typically configured to process the acquired echo signals and extract quadrature components (i.e., I,Q data) of the echo signals. The quadrature components may be coupled in parallel paths to one or more processors (e.g., a B-mode processor, a Doppler processor, a Vector Flow processor) to extract relevant information (e.g., amplitude, Doppler shift estimates, velocity vector estimates, etc.) for producing different types of ultrasound images (e.g., B-mode images, color, power or spectral Doppler images, vector flow images, etc.).

In accordance with the examples herein, the process 900 may involve generating one or more grayscale (B-mode) images of the bodily structure (e.g., a vessel), as shown in block 902. Concurrently, as shown in block 904, beam-angle-independent velocity estimates (i.e., axial, lateral and/or elevational velocity components) of the fluid flowing through the bodily structure may be obtained by a vector flow processor. The axial and lateral velocity estimates, and in the case of three-dimensional (3D) imaging the elevational, velocity estimates may be used to produce vector flow images (e.g., a visualization of the velocity vector field), as shown in block 906. According to principles of the present invention, the beam-angle-independent velocity estimates may be used to produce a flow direction map, as shown in block 908. The flow direction map may be visual representation of the flow directions for every spatial location within a flow region (e.g., the region inside the bodily structure that contains the fluid). In some examples, the flow direction associated with every location in the flow region may be encoded in color and presented as a flow direction map (e.g., examples of which are shown in FIGS. 3-6). The process may continue by displaying one or more ultrasound images which include graphical representations of the beam-angle-independent velocity estimates overlaid on background images of the anatomy (e.g., B-mode images), as shown in block 910. This may involve displaying one or more overlay images that include vector flow maps or color maps (e.g., flow direction color maps). In some examples, the overlay ultrasound images may be dynamically updated in real-time. That is, in the case of the flow direction color map overlays, both the background B-mode image and the color overlay may be updated in real time, synchronously using the same refresh rate. In other examples, different refresh rates may apply to the two components of the overlay image, as may be appropriate based on computational resources.

The process may continue by the system the receiving of a selection of a region of interest (ROI), which in some cases may be user-selected, as shown in block 916 or may be automatically-defined by the system, as shown in block 914. As described herein, the system may be configured to automatically identify a suspicious region by performing statistical analysis, as shown in block 912. The system may identify one or more regions exhibiting flow variability based on the statistical analysis and may designate the subset of pixels associated with greatest amount of flow variability as the ROI. In some examples, multiple ROIs may be identified based on having identified multiple sub-regions associated with flow variability and these may be ranked and displayed along with the quantitative information (e.g., histograms) in sequence of diminishing severity. In some cases, the processor may employ thresholding to exclude variability below a certain level from being designated as suspicious. Regardless of the method used to identify an ROI, the process may continue by generating and displaying graphical representations of quantitative information about the flow within the selected ROI. For example, histograms of the flow direction, velocity magnitude, combinations of the two, or statistical measures of variability or combinations of the statistical measures with the velocity parameters, may be displayed in either 2D or 3D fashion, as shown in block 918. In some cases, the method may involve further user input to re-define quantification parameters, e.g., as shown in block 920. For example, the user may select additional ROIs, move or resize a current ROI, redefine temporal averaging windows, threshold parameters, etc. In some examples, the system may also display an ROI indicator (also referred to as statistical analysis box), which provides feedback to the user as to the region that is being interrogated.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A system for visualization and quantification of ultrasound imaging data, the system comprising:
    a display unit;
    a processor communicatively coupled to the display unit and to an ultrasound imaging apparatus for generating an image from ultrasound data representative of a bodily structure and fluid flowing within the bodily structure, wherein the processor is configured to:
    estimate axial and lateral velocity components of the fluid flowing within the bodily structure;
    determine a plurality of flow directions within the image based on the axial and lateral velocity components, the flow directions each defining an angle;
    automatically identifying a flow region comprising flow directions of statistical significance based on a statistical analysis indicative of the flow region having flow variability; and
    responsive to the identifying, cause the display unit to display the image including the bodily structure and the statistically significant flow region automatically identified.

2. The system of claim 1, wherein the statistical significance comprises a moving average, a standard deviation, or both of flow directions within a flow region that exceed or meet a threshold.

3. The system of claim 1 further comprising concurrently displaying a histogram of flow direction within the identified flow region.

4. The system of claim 3, wherein the histogram is a 2D or a 3D histogram of flow directions and flow direction velocities within.

5. A non-transitory computer-readable medium comprising executable instructions, which when executed cause a processor of a medical imaging system to display ultrasound imaging data by:
    generating an image from ultrasound data representative of a bodily structure and fluid flowing within the bodily structure;
    estimating axial and lateral velocity components of the fluid flowing within the bodily structure;
    determining a plurality of flow directions within the image based on the axial and lateral velocity components;
    differentially encoding the flow directions based on flow direction angle to generate a flow direction map;
    performing, by a processor, statistical analysis on the flow directions, and wherein a region of interest (ROI) is automatically selected by the processor based on the statistical analysis indicative of the ROI having flow variability; and
    displaying the image including the bodily structure overlaid with the flow direction map.

6. The non-transitory computer-readable medium of claim 5, further comprising receiving the selection of the ROI within a flow region and displaying additional quantitative information about the flow directions within the ROI.

7. The non-transitory computer-readable medium of claim 6, wherein the displaying additional quantitative information about the flow directions within the ROI comprises displaying a histogram of the flow directions within the ROI or a statistical measure of variability of the flow directions within the ROI.

8. The non-transitory computer-readable medium of claim 6, wherein the displaying additional quantitative information comprises displaying a histogram displaying at least two of the flow directions for pixels within the ROI, velocity magnitudes for pixels within the ROI, and a statistical measure of variability of either the flow directions or velocity magnitudes associated with the ROI.

9. The non-transitory computer-readable medium of claim 6, further comprising displaying, concurrently with the image, another image including a B-mode background image overlaid with vector map of the axial and lateral velocity components.

* * * * *